United States Patent [19]

Hornik et al.

[11] Patent Number: 5,770,687
[45] Date of Patent: Jun. 23, 1998

[54] COMFORMATIONALLY CONSTRAINED BACKBONE CYCLIZED SOMATOSTATIN ANALOGS

[75] Inventors: Vered Hornik, Rebovot; Alon Seri-Levy, Jerusalem; Gary Gellerman, Jerusalem; Chaim Gilon, Jerusalem, all of Israel

[73] Assignees: Peptor Limited, Rehovot; Yissim Research Development Co. of Hebrew University of Jerusalem, Jerusalem, both of Israel

[21] Appl. No.: 690,090

[22] Filed: Jul. 31, 1996

Related U.S. Application Data

[63] Continuation-in-part of Ser. No. 488,159, Jun. 7, 1995, and Ser. No. 569,042, Dec. 7, 1995.

[51] Int. Cl.[6] .................. C07K 7/64; A61K 38/04; A61K 38/12
[52] U.S. Cl. ............... 530/311; 530/317; 530/328; 514/9; 514/11; 514/15; 514/16
[58] Field of Search .................. 530/311, 317; 514/9, 11, 15, 16

[56] References Cited

U.S. PATENT DOCUMENTS

| | | | |
|---|---|---|---|
| 3,988,304 | 10/1976 | Garsky | 260/78 A |
| 4,011,182 | 3/1977 | Sarantakis | 260/8 |
| 4,054,558 | 10/1977 | Garsky | 260/112.5 S |
| 4,187,217 | 2/1980 | Chipens et al. | 260/112.5 R |
| 4,235,886 | 11/1980 | Freidinger et al. | 424/177 |
| 4,310,518 | 1/1982 | Freidinger et al. | 424/177 |
| 5,364,851 | 11/1994 | Joran | 530/345 |
| 5,371,070 | 12/1994 | Koerber et al. | 514/9 |

FOREIGN PATENT DOCUMENTS

| | | |
|---|---|---|
| 0 334 244 | 9/1989 | European Pat. Off. . |
| 0 336 779 | 10/1989 | European Pat. Off. . |
| 0 370 453 | 5/1990 | European Pat. Off. . |
| 0395417 | 10/1990 | European Pat. Off. . |
| 0 564 739 | 10/1993 | European Pat. Off. . |
| 0564739 | 10/1993 | European Pat. Off. . |
| 2304352 | 10/1976 | France . |
| 2411828 | 7/1979 | France . |
| 41 19 544 | 10/1992 | Germany . |
| WO 89/01781 | 3/1989 | WIPO . |
| WO 92/00091 | 1/1992 | WIPO . |
| WO 92/22566 | 12/1992 | WIPO . |
| WO 93/031206 | 1/1993 | WIPO . |
| WO 94/11393 | 5/1994 | WIPO . |
| WO 95/01800 | 1/1995 | WIPO . |

OTHER PUBLICATIONS

G. Greiner et al., "Synthesis of New Backbone–Cyclized Bradykinin Analogs", Pept. 1994, Proc.Eur.Pept.Symp. 23rd Meeting Date 1994, 289–290.

J. Krstenansky et al., "Cyclic hexapeptide antagonists of the bradykinin $B_2$ receptor: Receptor binding and solution backbone confirmation", *Letters in Peptide Science*, vol. 1 (1994) pp. 229–234.

Bell & Reisine, 1993, "Molecular biology of somatostatin receptors", TINS 16:34–38.

Brazeau et al, 1973, "Hypothalamic polypeptide that inhibits the secretion of immunoreactive pituitary growth hormone", *Science* 179:77–79.

Buscail et al., 1995, "Inhibition of cell proliferation by the somatostatin analogue RC–160 is mediated by somatostatin receptor subtypes SSTR2 and SSTR5 through different mechanisms", *Proc. Natl. Acad. Sci. USA* 92:1580–1584.

Byk & Gilon, 1992, "Building units for N–backbone cyclic peptides. 1. Synthesis of protected N–(ω–aminoalkylene)amino acids and their incorporation into dipeptide units", *J. Org. Chem.* 57:5687–5692.

Charpentier et al., 1989, "Synthesis and binding affinities of cyclic and related linear analogues of $CCK_8$ selective for central receptors", *J. Med. Chem.* 32:1184–1190.

Giannis & Kolter, 1993, "Peptidomimetics for receptor ligands —Discovery, development, and medical perspectives", *Angew. Chem. Int. Ed. Engl.* 32:1244–1267.

Gilon et al., 1992, "SAR studies of cyclosepitide: Effects of cyclization and charge at position 6", *Chem. Biol.* Proc Am Pept Symp 12th. pp. 476–477.

Gilon et al., 1991, "Backbone cyclization: A new method for conferring conformational constraint on peptides", *Biopolymers* 31:745–750.

Hruby et al., 1990, "Emerging approaches in the molecular design of receptor–selective peptide ligands: conformational, topographical and dynamic considerationsa", *Biochem. J.* 268:249–262.

Lamberts et al., 1990, "Somatostatin–receptor imaging in the localization of endocrine tumors", *New England J. Med.* 323:1246–1249.

Lamberts, 1988, "The role of somatostatin in the regulation of anterior pituitary hormone secretion and the use of its analogs in the treatment of human pituitary tumors", *Endocrine Reviews* 9:4517–435.

Lymangrover & Keku, 1983, "Varying the duration of A23187 administration alters its effect on adrenal steroidogenesis", *Life Sciences* 34:371–377.

Mosberg et al., 1983, "Bis–penicillamone enkephalins posses highly improved specificity toward δ opioid receptors", *Proc. Natl. Acad. Sci. USA* 80:5871–5874.

Plotsky & Vale, 1985, "Patterns of growth hormone–releasing factor and somatostatin secretion into the hypophysial–portal circulation of the rat", *Science* 230:461–463.

(List continued on next page.)

*Primary Examiner*—Cecilia J. Tsang
*Assistant Examiner*—Anish Gupta
*Attorney, Agent, or Firm*—Pennie & Edmonds LLP

[57] ABSTRACT

Novel peptide analogs are disclosed. The novel peptides are conformationally constrained backbone cyclized somatostatin analogs. Methods for synthesizing the somatostatin analogs and for producing libraries of the somatostatin analogs are also disclosed. Furthermore, pharmaceutical compositions comprising somatostatin analogs, and methods of using such compositions in the treatment of endocrine disorders, neoplasms and metabolic disorders are also disclosed.

17 Claims, 3 Drawing Sheets

OTHER PUBLICATIONS

Raynor et al., 1993, "Cloned somatostatin receptors: Identification of subtyoe–selective peptides and demonstration of high affinity binding of linear peptides", *Mol. Pharmacol.* 43:838–844.

Reisine & Bell, 1995, "Molecular biology of somatostatin receptors", *Endocrine Reviews* 16:427–442.

Reubi et al., "Multiple actions of somatostatin in neoplastic disease", *TIPS* 16;110–115.

Rizo et al., 1992, "Constrained peptides: Models of bioactive peptides and protein substructures", *Annu. Rev. Biochem.* 61:387–418.

Rodriguez et al., 1990, "Synthesis of cyclic analogues of cholecystokinin highly selective for central receptors", *Int. J. Peptide Protein Res.* 35:441–451.

Steranka et al., 1988, "Bradykinin as a pain mediator: Receptors are localized to sensory neurons, and antagonists have analgesic actions", *Proc. Natl. Acad. Sci. USA* 85:3245–3249.

Veber et al., 1984, "A super active cyclic hexapeptide of somatostatin", *Life Sciences* 34:1371–1378.

Veber et al., 1985, "The design of metabolucally–stable peptide analogs", *TINS* pp. 392–396.

R.N. Zuckerman, 1993, "The chemical synthesis of peptidomimetic libraries",*Current Opinion in Structural Biol.* 3:580–584.

Gilon et al. "Backbone cyclization: A new Method for Conferring Conformatioanl Constraint on Peptides", Biopolymers, vol. 31, pp. 745–750, 1991.

Byk et al. "Builing Units for N–Bacbone Cyclic Peptides. 1. Synthesis of Protected N–(–aminoalkylene) Amino Acids and Their Incorporation Into Dipeptide Units", J. Org. Chem., vol. 57, pp. 5687–5692, 1992.

Raynor et al. "Coloned Somatostatin Receptors: Identification of Subtype Selective Peptides and Demonstration of High Affinity Binding of Linear Peptides" Molecular Pharmacology, vol. 43, pp. 838–844, 1993

Rudinger, J. "Characteristics of the Amino Acids as Components of a Peptide Hormone Sequence" in Peptide Hormones (ed. J. A. Parsons). University Park Press, Baltimore, pp. 1–7, 1976.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Ala  Gly  Cys  Lys  Asn  Phe  Phe  Trp  Lys  Thr  Phe  Thr  Ser  Cys
    1                   5                        10

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="2-Nal or Absent"

( i x ) FEATURE:
        ( A ) NAME/KEY: Modified-site
        ( B ) LOCATION: 2
        ( D ) OTHER INFORMATION: /product="Phe, Gly, or Ala"

( i x ) FEATURE:
        ( A ) NAME/KEY: Modified-site
        ( B ) LOCATION: 3
        ( D ) OTHER INFORMATION: /product="pNH2Phe"

( i x ) FEATURE:
        ( A ) NAME/KEY: Modified-site
        ( B ) LOCATION: 7
        ( D ) OTHER INFORMATION: /product="Phe, Gly, or Ala"

( i x ) FEATURE:

( A ) NAME/KEY: Modified-site
( B ) LOCATION: 8
( D ) OTHER INFORMATION: /product="Thr, Val, Ala, bAla, or 2-Nal"

( x i ) SEQUENCE DESCRIPTION: SEQ ID NO:2:

Xaa Xaa Phe Trp Lys Gly Xaa Xaa
1                   5

( 2 ) INFORMATION FOR SEQ ID NO:3:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /product="Phe-N2"

( i x ) FEATURE:
( A ) NAME/KEY: Modified-site
( B ) LOCATION: 6
( D ) OTHER INFORMATION: /product="Phe-C3"

( i x ) FEATURE:
( A ) NAME/KEY: Modified-site
( B ) LOCATION: 7
( D ) OTHER INFORMATION: /product="Thr, Val, Ala, or bAla"

( x i ) SEQUENCE DESCRIPTION: SEQ ID NO:3:

Phe Phe Trp Lys Gly Phe Xaa
1                   5

( 2 ) INFORMATION FOR SEQ ID NO:4:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /product="Gly-N3"

( i x ) FEATURE:
( A ) NAME/KEY: Modified-site
( B ) LOCATION: 6
( D ) OTHER INFORMATION: /product="Gly-C2"

( x i ) SEQUENCE DESCRIPTION: SEQ ID NO:4:

Gly Trp Lys Thr Phe Gly Ser Phe
1                   5

( 2 ) INFORMATION FOR SEQ ID NO:5:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site (B) LOCATION: 2
                (D) OTHER INFORMATION: /product="Gly-N3"

(ix) FEATURE:
                (A) NAME/KEY: Modified-site
                (B) LOCATION: 7
                (D) OTHER INFORMATION: /product="Gly-C2"

(xi) SEQUENCE DESCRIPTION: SEQ ID NO:5:

Phe  Gly  Trp  Lys  Thr  Phe  Gly  Ser
        1                   5

(2) INFORMATION FOR SEQ ID NO:6:

(i) SEQUENCE CHARACTERISTICS:
                (A) LENGTH: 8 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /product="Gly-N3"

(ix) FEATURE:
                (A) NAME/KEY: Modified-site
                (B) LOCATION: 6
                (D) OTHER INFORMATION: /product="Gly-C2"

(xi) SEQUENCE DESCRIPTION: SEQ ID NO:6:

Gly  Phe  Phe  Trp  Lys  Gly  Phe  Thr
        1                   5

(2) INFORMATION FOR SEQ ID NO:7:

(i) SEQUENCE CHARACTERISTICS:
                (A) LENGTH: 8 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 2
                (D) OTHER INFORMATION: /product="Gly-N3"

(ix) FEATURE:
                (A) NAME/KEY: Modified-site
                (B) LOCATION: 7
                (D) OTHER INFORMATION: /product="Gly-C2"

(xi) SEQUENCE DESCRIPTION: SEQ ID NO:7:

Lys  Gly  Phe  Phe  Trp  Lys  Gly  Phe
        1                   5

(2) INFORMATION FOR SEQ ID NO:8:

(i) SEQUENCE CHARACTERISTICS:
                (A) LENGTH: 8 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /product="Gly-N3"

( i x ) FEATURE:
  ( A ) NAME/KEY: Modified-site
  ( B ) LOCATION: 5
  ( D ) OTHER INFORMATION: /product="Gly-C2"

( x i ) SEQUENCE DESCRIPTION: SEQ ID NO:8:

Gly Lys Asn Phe Gly Trp Lys Thr
1               5

( 2 ) INFORMATION FOR SEQ ID NO:9:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 2
    ( D ) OTHER INFORMATION: /product="Gly-N3"

( i x ) FEATURE:
    ( A ) NAME/KEY: Modified-site
    ( B ) LOCATION: 6
    ( D ) OTHER INFORMATION: /product="Gly-C2"

( x i ) SEQUENCE DESCRIPTION: SEQ ID NO:9:

Gly Gly Lys Asn Phe Gly Trp Lys
1               5

( 2 ) INFORMATION FOR SEQ ID NO:10:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 3
    ( D ) OTHER INFORMATION: /product="Gly-N3"

( i x ) FEATURE:
    ( A ) NAME/KEY: Modified-site
    ( B ) LOCATION: 7
    ( D ) OTHER INFORMATION: /product="Gly-C2"

( x i ) SEQUENCE DESCRIPTION: SEQ ID NO:10:

Ala Gly Gly Lys Asn Phe Gly Trp
1               5

( 2 ) INFORMATION FOR SEQ ID NO:11:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 3
    ( D ) OTHER INFORMATION: /product="OTHER"
      / note= "Phe, Phe-N2, Phe-N3, Phe-C2, Phe-C3, pNO2Phe,
      pClPhe, pFPhe, Phg or L2Nal"

(ix) FEATURE:
    (A) NAME/KEY: Modified-site
    (B) LOCATION: 4
    (D) OTHER INFORMATION: /product="OTHER"
        / note= "Phe, Phe-N2, Phe-N3, Phe-C2, Phe-C3, pNO2Phe
        -- OR --"

(ix) FEATURE:
    (A) NAME/KEY: Modified-site
    (B) LOCATION: 4
    (D) OTHER INFORMATION: /product="OTHER"
        / note= "pClPhe, pFPhe, Phg or L2Nal"

(ix) FEATURE:
    (A) NAME/KEY: Modified-site
    (B) LOCATION: 7
    (D) OTHER INFORMATION: /product="OTHER"
        / note= "Phe-N2, Phe-N3, Phe-C2 or Phe-C3"

(xi) SEQUENCE DESCRIPTION: SEQ ID NO:11:

Lys Asn Xaa Xaa Trp Lys Thr Phe
1                         5

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product="Phe-N2, Phe-N3, Lys-N2
          or Gly-N2"

(ix) FEATURE:
        (A) NAME/KEY: Modified-site
        (B) LOCATION: 2
        (D) OTHER INFORMATION: /product="Phe or Tyr"

(ix) FEATURE:
        (A) NAME/KEY: Modified-site
        (B) LOCATION: 7
        (D) OTHER INFORMATION: /product="Thr, Val or bAla"

(ix) FEATURE:
        (A) NAME/KEY: Modified-site
        (B) LOCATION: 6
        (D) OTHER INFORMATION: /product="Phe-C3"

(xi) SEQUENCE DESCRIPTION: SEQ ID NO:12:

Xaa Xaa Trp Lys Gly Phe Xaa
1                    5

COMFORMATIONALLY CONSTRAINED BACKBONE CYCLIZED SOMATOSTATIN ANALOGS

CROSS-REFERENCE TO RELATED APPLICATIONS

This application is a continuation-in-part of applications Ser. Nos. 08/488,159 filed Jun. 7, 1995 and 08/569,042 filed Dec. 7, 1995.

FIELD OF THE INVENTION

The present invention relates to conformationally constrained $N^\alpha$ backbone-cyclized somatostatin analogs cyclized via novel linkages, to processes for the preparation of these backbone cyclized peptide analogs, to methods for using these peptide analogs and to pharmaceutical compositions containing same.

BACKGROUND OF THE INVENTION

Somatostatin analogs

Somatostatin is a cyclic tetradecapeptide found both in the central nervous system and in peripheral tissues. It was originally isolated from mammalian hypothalamus and identified as an important inhibitor of growth hormone secretion from the anterior pituitary. Its multiple biological activities include inhibition of the secretion of glucagon and insulin from the pancreas, regulation of most gut hormones and regulation of the release of other neurotransmitters involved in motor activity and cognitive processes throughout the central nervous system (for review see Lamberts, *Endocrine Rev.*, 9:427, 1988). Additionally, somatostatin and its analogs are potentially useful antiproliferative agents for the treatment of various types of tumors.

Natural somatostatin (also known as Somatotropin Release Inhibiting Factor, SRIF) of the following structure: H-Ala$^1$-Gly$^2$-Cys$^3$-Lys$^4$-Asn$^5$-Phe$^6$-Phe$^7$-Trp$^8$-Lys$^9$-Thr$^{10}$-Phe$^{11}$-Thr$^{12}$-Ser$^{13}$-Cys$^{14}$ -OH (SEQ ID NO:1was first isolated by Guillemin and colleagues (Bruzeau et al. *Science*, 179:78, 1973). It exerts its effect by interacting with a family of receptors. Recently five receptor subtypes, termed SSTR1-5, have been identified and cloned. In its natural form, somatostatin has limited use as a therapeutic agent since it exhibits two undesirable properties: poor bioavailability and short duration of action. For this reason, great efforts have been made during the last two decades to find somatostatin analogs that will have superiority in either potency, biostability, duration of action or selectivity with regard to inhibition of the release of growth hormone, insulin or glucagon.

Structure-activity relation studies, spectroscopic techniques such as circular dichroism and nuclear magnetic resonance, and molecular modeling approaches reveal the following: the conformation of the cyclic part of natural somatostatin is most likely to be an antiparallel β-sheet; Phe$^6$ and Phe$^{11}$ play an important role in stabilizing the pharmacophore conformation through hydrophobic interactions between the two aromatic rings; the four amino acids Phe$^7$ -Trp$^9$-Lys$^9$-Thr$^{10}$ which are spread around the β-turn in the antiparallel β-sheet are essential for the pharmacophore; and (D)Trp$^8$ is preferable to (L)Trp$^8$ for the interactions with somatostatin receptor subtypes 2 through 5.

Nevertheless, a hexapeptide somatostatin analog containing these four amino acids anchored by a disulfide bridge:

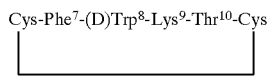

is almost inactive both in vitro and in vivo, although it has the advantage of the covalent disulfide bridge which replaces the Phe$^6$-Phe$^{11}$ hydrophobic interactions in natural somatostatin.

Four main approaches have been attempted in order to increase the activity of this hexapeptide somatostatin analog. (1) Replacing the disulfide bridge by a cyclization which encourages a cis-amide bond, or by performing a second cyclization to the molecule yielding a bicyclic analog. In both cases the resultant analog has a reduced number of conformational degrees of freedom. (2) Replacing the original residues in the sequence Phe$^7$-(D)Trp$^8$-Lys$^9$-Thr$^{10}$ with other natural or non-natural amino acids, such as replacing Phe$^7$ with Tyr$^7$ and Thr$^{10}$ with Val$^{10}$. (3) Incorporating additional functional groups from natural somatostatin with the intention that these new elements will contribute to the interaction with the receptor. (4) Eliminating one of the four amino acids Phe$^7$-(D)Trp$^8$-Lys$^9$-Thr$^{10}$ with the assumption that such analogs would be more selective.

The somatostatin analog, MK-678: cyclo (N-Me-Ala$^6$-Tyr$^7$- (D) Trp$^8$-Lys$^9$-Val$^{10}$-Phe) is an example of a highly potent somatostatin analog designed using the first three approaches above (Veber, et al., *Life Science*, 34:371, 1984). In this hexapeptide analog, a cis-amide bond is located between N-Me-Ala and Phe$^{11}$, Tyr$^7$ and Val$^{10}$ replace Phe$^7$ and Thr$^{10}$ respectively, and Phe$^{11}$ is incorporated from natural somatostatin.

Another group of somatostatin analogs (U.S. Pat. Nos. 4,310,518 and 4,235,886) includes Octreotide:

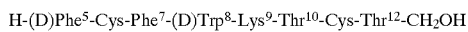

the only approved somatostatin analog currently available. It was developed using the third approach described above. Here, (D)Phe$^5$ and the reduced C-terminal Thr$^{12}$-CH$_2$OH are assumed to occupy some of the conformational space available to the natural Phe$^6$ and Thr$^{12}$, respectively.

The compound TT-232:

is closely related to Octreotide and is an example of implementing the fourth approach described above. The lack of Thr$^{10}$ is probably responsible for its high functional selectivity in terms of antitumor activity.

These examples of highly potent somatostatin analogs suggest that the phenylalanines in positions 6 and 11 not only play an important role in stabilizing the pharmacophore conformation but also have a functional role in the interaction with the receptor. It is still an open question whether one phenylalanine (either Phe$^6$ or Phe$^{11}$) is sufficient for the interaction with the receptor or whether both are needed.

It is now known that the somatostatin receptors constitute a family of five different receptor subtypes (Bell and Reisine, *Trends Neurosci.*, 16, 34–38, 1993), which may be distinguished on the basis of their tissue specificity and/or biological activity. Somatostatin analogs known in the art may not provide sufficient selectivity or receptor subtype selectivity, particularly as anti-neoplastic agents (Reubi and Laissue, *TIPS*, 16, 110–115, 1995).

Symptoms associated with metastatic carcinoid tumors (flushing and diarrhea) and vasoactive intestinal peptide (VIP) secreting adenomas (watery diarrhea) are treated with somatostatin analogs. Somatostatin has been also approved for the treatment of severe gastrointestinal hemorrhages. Somatostatin may also be useful in the palliative treatment of other hormone-secreting tumors (e.g., pancreatic islet-cell tumors and acromegaly) and hormone dependent tumors (e.g., chondrosarcoma and osteosarcoma) due to its anti-secretory activity.

Peptidomimetics

As a result of major advances in organic chemistry and in molecular biology, many bioactive peptides can now be prepared in quantities sufficient for pharmacological and clinical utilities. Thus in the last few years new methods have been established for the treatment and therapy of illnesses in which peptides have been implicated. However, the use of peptides as drugs is limited by the following factors: a) their low metabolic stability towards proteolysis in the gastrointestinal tract and in serum; b) their poor absorption after oral ingestion, in particular due to their relatively high molecular mass or the lack of specific transport systems or both; c) their rapid excretion through the liver and kidneys; and d) their undesired side effects in non-target organ systems, since peptide receptors can be widely distributed in an organism.

Moreover, with few exceptions, native peptides of small to medium size (less than 30 amino acids) exist unordered in dilute aqueous solution in a multitude of conformations in dynamic equilibrium which may lead to lack of receptor selectivity, metabolic susceptibilities and hamper attempts to determine the biologically active conformation. If a peptide has the biologically active conformation per se, i.e., receptor-bound conformation, then an increased affinity toward the receptor is expected, since the decrease in entropy on binding is less than that on the binding of a flexible peptide. It is therefore important to strive for and develop ordered, uniform and biologically active peptides.

In recent years, intensive efforts have been made to develop peptidomimetics or peptide analogs that display more favorable pharmacological properties than their prototype native peptides. The native peptide itself, the pharmacological properties of which have been optimized, generally serves as a lead for the development of these peptidomimetics. However, a major problem in the development of such agents lies in determining the active region of a biologically active peptide. For instance, frequently only a small number of amino acids (usually four to eight) are responsible for the recognition of a peptide ligand by a receptor. Once this biologically active site is determined a lead structure for development of peptidomimetic can be optimized, for example by structure-activity relationship studies.

As used herein, a "peptidomimetic" is a compound that, as a ligand of a receptor, can imitate (agonist) or block (antagonist) the biological effect of a peptide at the receptor level. The following factors should be considered to achieve the best possible agonist peptidomimetic a) metabolic stability, b) good bioavailability, c) high receptor affinity and receptor selectivity, and d) minimal side effects.

A generally applicable and successful method recently has been the development of conformationally restricted peptidomimetics that imitate the receptor-bound conformation of the endogenous peptide ligands as closely as possible (Rizo and Gierasch, *Ann. Rev. Biochem.*, 61:387, 1992). Investigations of these types of analogs show them to have increased resistance toward proteases, that is, an increase in metabolic stability, as well as increased selectivity and thereby fewer side effects (Veber and Friedinger, *Trends Neurosci.*, p. 392, 1985).

Once these peptidomimetic compounds with rigid conformations are produced, the most active structures are selected by studying the structure-activity relationships. Such conformational constraints can involve local modifications of structure or global conformational restraints (for review see Giannis and Kolter, *Angew. Chem. Int. Ed. Engl.* 32:1244, 1993).

Conformationally constrained peptide analogs

Bridging between two neighboring amino acids in a peptide leads to a local conformational modification, the flexibility of which is limited in comparison with that of regular dipeptides. Some possibilities for forming such bridges include incorporation of lactams and piperazinones. γ-Lactams and δ-lactams have been designed to some extent as "turn mimetics"; in several cases the incorporation of such structures into peptides leads to biologically active compounds.

Global restrictions in the conformation of a peptide are possible by limiting the flexibility of the peptide strand through cyclization (Hruby et al., *Biochem. J.*, 268:249, 1990). Not only does cyclization of bioactive peptides improve their metabolic stability and receptor selectivity, cyclization also imposes constraints that enhance conformational homogeneity and facilitates conformational analysis. The common modes of cyclization are the same found in naturally occurring cyclic peptides. These include side chain to side chain cyclization or side chain to end-group cyclization. For this purpose, amino acid side chains that are not involved in receptor recognition are connected together or to the peptide backbone. Another common cyclization is the end-to-end cyclization.

The main limitations to these classical modes of cyclization are that they require substitution of amino acid side chains in order to achieve cyclization.

Another conceptual approach to the conformational constraint of peptides was introduced by Gilon, et al., (*Biopolymers* 31:745, 1991) who proposed backbone to backbone cyclization of peptides. The theoretical advantages of this strategy include the ability to effect cyclization via the carbons or nitrogens of the peptide backbone without interfering with side chains that may be crucial for interaction with the specific receptor of a given peptide. While the concept was envisaged as being applicable to any linear peptide of interest, in point of fact the limiting factor in the proposed scheme was the availability of suitable building units that must be used to replace the amino acids that are to be linked via bridging groups. The actual reduction to practice of this concept of backbone cyclization was prevented by the inability to devise any practical method of preparing building units of amino acids other than glycine (Gilon et al., *J. Org. Chem*, 57:5687, 1992). When syntheses of analogs of other amino acids were attempted the method used was unsuccessful or of such low yield as to preclude any general applicability.

In Gilon, EPO Application No. 564,739 A2; and *J. Org. Chem.*, 57:5687, 1992, two basic approaches to the synthesis of building units are described. The first starts with the reaction of a diamine with a bromo acid. Selective protection of the ω amine and further elaboration of protecting groups provides a building unit, suitable for Boc chemistry peptide synthesis. The second approach starts with selective protection of a diamine and reaction of the product with chloro-acetic acid to provide the protected glycine derivative, suitable for Fmoc peptide synthesis.

Both examples deal with the reaction of a molecule of the general type X-CH(R)—CO—OR' (wherein X represents a leaving group which, in the examples given, is either Br or Cl) with an amine which replaces the X. The amine bears an alkylidene chain which is terminated by another functional group, amine in the examples described, which may or may not be blocked by a protecting group.

In all cases the α nitrogen of the end product originates in the molecule which becomes the bridging chain for subsequent cyclization. This approach was chosen in order to take advantage of the higher susceptibility to nucleophilic displacement of a leaving group next to a carboxylic group.

In a molecule where R is different than hydrogen there is a high tendency to eliminate HX under basic conditions. This side reaction reduces the yield of Gilon's disclosed method to the point where it is impractical for production of building units based on amino acids other than glycine. The diamine nitrogen is primary while the product contains a secondary nitrogen, which is a better nucleophile. So while the desired reaction is generally sluggish, and requires the addition of catalysts, the product is commonly contaminated with double alkylation products. There is no mention of building units with end group chemistries other than nitrogen, so the only cyclization schemes possible are backbone to side chain and backbone to C terminus.

Libraries of backbone cyclized peptide analogs

As mentioned above linear peptides suffer from several serious drawbacks as potential drugs, inasmuch as they are notoriously unstable in vivo, often lack high affinity of binding to their receptor, frequently lack selectively to one kind of receptor, and generally have poor oral bioavailability. In efforts to overcome such problems, it is also possible to utilize the methodologies developed in connection with synthetic peptide libraries to generate collections of cyclic peptides, novel biopolymers and even novel branched oligomeric compounds (reviewed by Zuckermann, Current Opinion in Structural Biology 3, 580–584, 1993).

The generation of libraries of cyclic peptides requires that in addition to any previously stated considerations, the cyclization reaction be performed in a high yield and with a minimum of additional manipulations. Unfortunately, classical cyclization reactions are highly sequence dependent in terms of the expected yields, making the uniform cyclization of a peptide mixture unreliable.

Recent advances in the cyclization of peptides directly on the solid support have improved the synthetic procedure, and even allowed the automation of cyclization reactions based on known cyclization schemes. In the past, cyclizations were typically performed in solution under conditions of high dilution. Polymer-supported cyclizations can both avoid potential side reactions such as oligomerization and facilitate product purification. For example, on-resin cyclization methods have recently been used to prepare cyclopeptides with bridges formed of thioethers, disulfides, or lactams between two side chains, lactam between the amino terminus and a side chain, and lactams between the amino and carboxy termini (reviewed by Zuckermann, Current Opinion in Structural Biology 3, ibid).

The use of resin-bound cyclic peptides and free cyclic peptides in combinatorial libraries is disclosed in WO 92/00091. However, these cyclic peptides do not contain any conformationally constraining element, and in cases where cyclization is achieved, these peptides may still adopt a number of conformations and suffer many of the same shortcomings as linear peptides.

Cyclic semi-random peptide libraries, disclosed in WO 95/01800, are exclusively cyclic penta- and hexa-peptide libraries containing one or more randomized amino acids and a conformationally constraining element in the form of an amino acid residue such as proline which fixes the beta turn angles of the adjacent amino acid residues. The advantages of such conformationally constraining elements is stressed by the inventors of this approach. However, inclusion of such elements via incorporation of a particular amino acid residue into the peptide sequence may have detrimental effects on those residues required for receptor recognition or other biological activity. Furthermore, in that disclosure (WO 95/01800), the cyclization reaction is merely another coupling reaction in which the terminal amino group of the linear peptide is coupled to the terminal carboxy group of the peptide.

SUMMARY OF THE INVENTION

According to the present invention, novel peptidomimetic compounds, which are characterized in that they incorporate novel building units with bridging groups attached to the alpha nitrogens of alpha amino acids; have now been generated.

The most striking advantages of this approach are: 1) The method enables cyclization of the peptide sequence without compromising any of the side chains of the peptide thereby decreasing the chances of sacrificing functional groups essential for biological recognition and function. 2) The method allows optimization of the peptide conformation by allowing permutation of the bridge length, direction, and bond type (e.g., amide, disulfide, thioether, thioester, etc.) and position of the bond in the ring. 3) When applied to cyclization of linear peptides of known activity, the bridge can be designed in such a way as to minimize interaction with the active region of the peptide and its cognate receptor. This decreases the chances of the cyclization arm interfering with recognition and function, and also creates a site suitable for attachment of tags such as radioactive tracers, cytotoxic drugs, light capturing substances, or any other desired label.

The newly generated libraries, disclosed according to the present invention, now enable varying conformation as well as level of flexibility (constraint) in order to find the optimal backbone conformation of the peptide in performing its role as an agonist or antagonist. This is accomplished by varying both the position of the bridgeheads (i.e., the positions in the linear sequence of residues that are to be cyclized), as well as varying the length, the direction and the bond type of the bridge between these units.

It is another object of the present invention to provide backbone cyclized somatostatin analogs that comprise peptide sequences which contain one nitrogen atom of the peptide backbone connected to a bridging group, as described below. In the present invention, one or more pairs of the building units is joined together to form a cyclic structure. Thus, according to one aspect of the present invention, backbone cyclized somatostatin analogs are provided that have the general Formula (I):

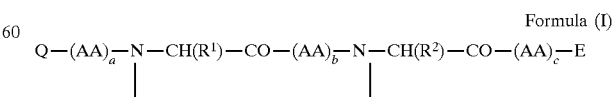

Formula (I)

wherein: a–c each independently designates an integer from 1 to 8 or zero; (AA) designates an amino acid residue wherein the amino acid residues in each chain may be the same or different; Q represents H or an acyl group; E represents a hydroxyl group, a carboxyl protecting group or an amino group, or the terminal carboxyl group can be reduced to $CH_2$—OH; $R^1$ and $R^2$ each designates an amino acid side-chain optionally bound with a specific protecting group; and the line designates a bridging group of the Formula:

(i) —X—M—Y—W—Z—; or (ii) —X—M—Z— wherein: M and W are independently selected from the group consisting of amide, thioether, thioester and disulfide; and X, Y and Z are each independently selected from the group consisting of alkylene, substituted alkylene, arylene, homo- or hetero- cycloalkylene and substituted cycloalkylene.

In certain preferred embodiments, the terminal carboxyl group of Formula (I) is reduced to a $CH_2OH$ group.

Another embodiment of the present invention involves N-backbone to side chain cyclized somatostatin analogs of the general formula (II):

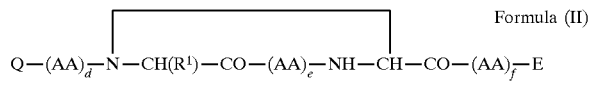

wherein: d–f each independently designates an integer from 1 to 8 or zero; (AA) designates an amino acid residue wherein the amino acid residues in each chain may be the same or different; Q represents H or an acyl group; E represents a hydroxyl group, a carboxyl protecting group or an amino group, or the terminal carboxyl group can be reduced to $CH_2OH$; $R^1$ designates an amino acid side-chain optionally bound with a specific protecting group; and the line designates a bridging group of the Formula: (i) —X—M—Y—W—Z—; or (ii) —X—M—Z— wherein M and W are independently selected from the group consisting of amide, thioether, thioester and disulfide; and X, Y and Z are each independently selected from the group consisting of alkylene, substituted alkylene, arylene, homo- or hetero-cycloalkylene and substituted cycloalkylene.

A preferred embodiment of the present invention involves the backbone cyclized somatostatin analog of Formulae I or II wherein the line designates a bridging group of the Formula —$(CH_2)_x$—M—$(CH_2)_y$—; M is selected from the group consisting of amide, thioether, thioester and disulfide; and x and y each independently designates an integer from 1 to 10.

Further preferred are backbone cyclized somatostatin analogs of the Formula I or II wherein $R^1$ and $R^2$ are other than H, such as $CH_3$, $(CH_3)_2CH$—, $(CH_3)_2CHCH_2$—, $CH_3CH_2CH(CH_3)$—, $CH_3S(CH_2)_2$—, $HOCH_2$—, $CH_3CH(OH)$—, $HSCH_2$—, $NH_2C(=O)CH_2$—, $NH_2C(=O)(CH_2)_2$—, $NH_2(CH_2)_3$—, $HOC(=O)CH_2$—, $HOC(=O)(CH_2)_2$—, $NH_2(CH_2)_4$—, $C(NH_2)_2 NH(CH_2)_3$—, HO—phenyl—$CH_2$—, benzyl, methylindole, and methylimidazole.

Another preferred aspect of the present invention is directed to backbone cyclization to generate novel somatostatin analogs linked between positions 6 and 11, leaving the phenylalanine side chains untouched. This conformational stabilization is much more rigid than the $Phe^6$, $Phe^{11}$ hydrophobic interaction in natural somatostatin and is more stable to reduction/oxidation reactions than the Cys-Cys disulfide bridge. In other words, for the first time a stable covalent bridge can be achieved while either one or both of the original $Phe^6$ and $Phe^{11}$ are retained.

Moreover, backbone cyclizations can also be used to anchor the β-turn, not only in positions 6 and 11 but also inside the active reaction of $Phe^7$-$(D)Trp^8$-$Lys^9$-$Thr^{10}$, yielding either a monocyclic analog with a preferable conformation or a very rigid bicyclic analog. Here again, the side chains of the pharmacologically active amino acids remain untouched and the only change is in limiting the conformational space.

As used herein and in the claims in the following more preferred backbone cyclized peptide analogs, the superscript numbers following the amino acids refer to their position numbers in the native Somatostatin.

A more preferred backbone cyclized peptide novel analog is the Formula (Va):

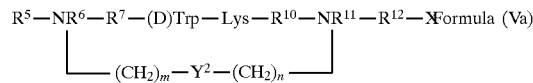

with a most preferred analog having Formula (Vb):

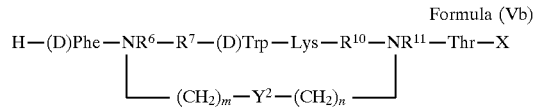

wherein m and n are 1 to 5; X designates a carboxy terminal amide or alcohol; $R^5$ is absent or is Gly, (D)- or (L)-Ala, (D)- or (L)-Phe, Nal and β-Asp(Ind); $R^6$ and $R^{11}$ are independently Gly or (D)- or (L)-Phe; $R^7$ is Phe or Tyr; $R^{10}$ is absent or is Gly, Abu, Thr or Val; $R^{12}$ is absent or is Val, Thr or Nal, and $Y^2$ is selected from the group consisting of amide, thioether, thioester and disulfide. In these monocyclic somatostatin analogs, a backbone cyclization replaces the $Cys^6$-$Cys^{11}$ disulfide bridge, leaving the phenylalanine side chains as in the natural somatostatin. Still more preferred is the analog wherein $Phe^7$ is replaced with $Tyr^7$ and $Thr^{10}$ is replaced with $Val^{10}$.

Other more preferred monocyclic analogs that anchor the molecule in positions inside the active region rather than in positions 6 and 11 are formulae VI (a and b) and VII (a–c):

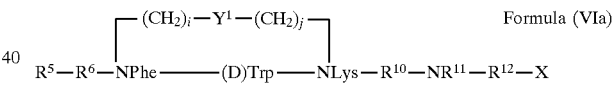

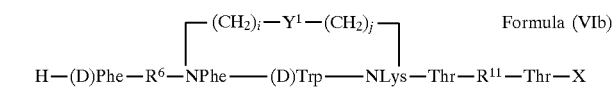

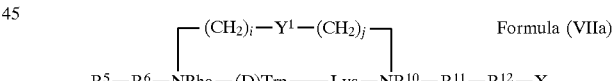

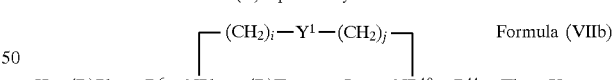

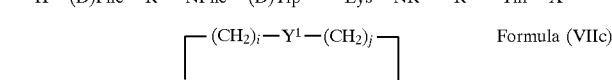

wherein i and j are independently 1 to 5; X designates a carboxy terminal amide or alcohol; $R^5$ is absent or is (D)- or (L)-Phe, Nal, or β-Asp(Ind); $R^6$ is (D) or (L)-Phe; $R^{10}$ is absent or is Gly, Abu or Thr; and $R^{11}$ is (D)- or (L)-Phe; $R1^2$ is absent or is Thr or Nal, and $Y^1$ is selected from the group consisting of amide, thioether, thioester and disulfide.

Still other more preferred analogs incorporate backbone cyclization in positions 6 and 11 as in Formula V, together with the backbone cyclizations as in Formula VI and VII, yielding rigid bicyclic analogs.

Other more preferred bicyclic analogs differ from Formulae V-VII by the replacement of the amino acids at positions 6 and 11 by cysteines which form a disulfide bond, leaving only one backbone cyclization in the Formulae VIII (a and b) and IX (a and b):

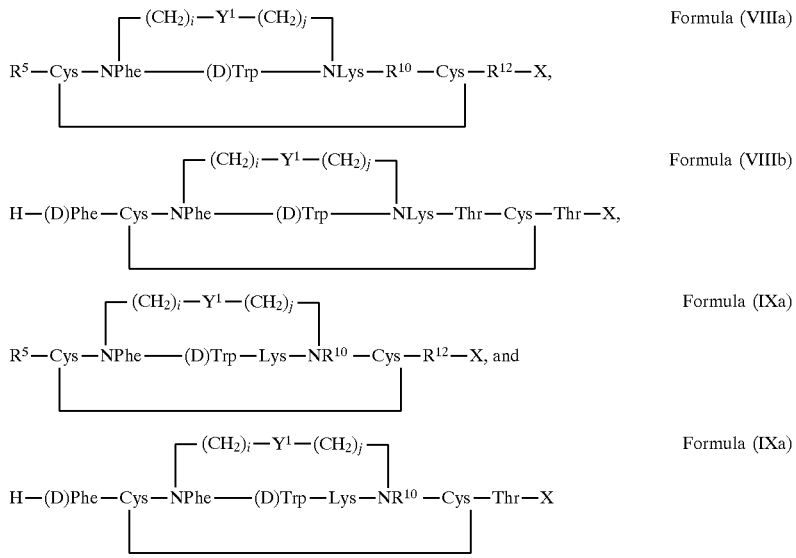

wherein i and j are independently 1 to 5; X designates a carboxy terminal amide or alcohol; $R^5$ is absent or is (D)- or (L)-Phe, Nal, or β-Asp (Ind); $R^6$ and $R^{11}$ are independently Gly or Phe; $R^{10}$ is absent or is Gly, Abu or Thr; $R^{12}$ is absent or is Thr or Nal; and $Y^1$ is selected from the group consisting of amide, thioether, thioester and disulfide.

The most preferred embodiments of the invention are currently:

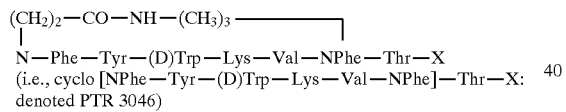
(i.e., cyclo [NPhe—Tyr—(D)Trp—Lys—Val—NPhe]—Thr—X: denoted PTR 3046)

and

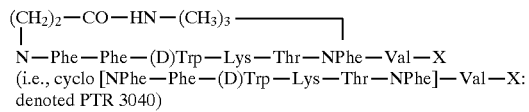
(i.e., cyclo [NPhe—Phe—(D)Trp—Lys—Thr—NPhe]—Val—X: denoted PTR 3040)

The most preferred monocyclic somatostatin analogs may also be prepared as libraries of active analogs, that are particularly useful to screen for the optimal conformers.

Libraries according to the present invention include compositions of the formulae X through XIV:

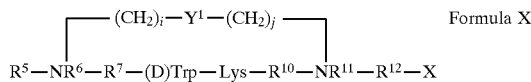

wherein i and j are independently 1 to 5; X designates a carboxy terminal amide or alcohol; $R^5$ is (D)Phe or 2-Nal; $R^6$ is Phe, Gly or Ala; $R^7$ is Tyr or pClPhe; $R^{10}$ is Thr, Val, Ser or Abu; $R^{11}$ is Phe, Gly or Ala; $R^{12}$ is Thr, Val, 2-Nal or (D)2-Nal, and $Y^1$ is selected from the group consisting of amide, thioether, thioester and disulfide.

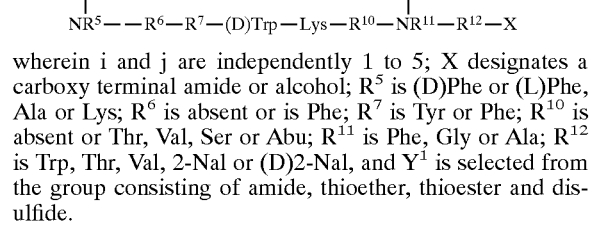

wherein i and j are independently 1 to 5; X designates a carboxy terminal amide or alcohol; $R^5$ is (D)Phe or (L)Phe, Ala or Lys; $R^6$ is absent or is Phe; $R^7$ is Tyr or Phe; $R^{10}$ is absent or Thr, Val, Ser or Abu; $R^{11}$ is Phe, Gly or Ala; $R^{12}$ is Trp, Thr, Val, 2-Nal or (D)2-Nal, and $Y^1$ is selected from the group consisting of amide, thioether, thioester and disulfide.

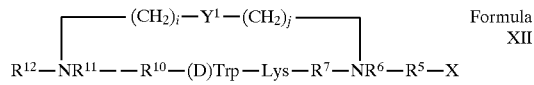

wherein i and j are independently 1 to 5; X designates a carboxy terminal amide or alcohol; $R^5$ Phe, (L)2-Nal or (D)2-Nal; $R^6$ is Phe, Gly or Ala; $R^7$ is (D)Phe, pCl(D)Phe, pNH$_2$Phe or (D)Tyr; $R^{10}$ is (D)Thr, (D)Val (D)Ala, (D)Leu or (D)Glu; $R^{11}$ is Phe, Gly or Ala; $R^{12}$ is absent or is Thr or Val; and $Y^1$ is selected from the group consisting of amide, thioether, thioester and disulfide.

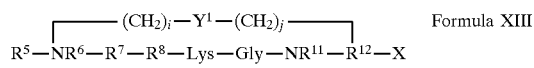

wherein i and j are independently 1 to 5; X designates a carboxy terminal amide or alcohol; $R^5$ is absent or (D)Phe or 2-Nal; R6 is Phe, Gly or Ala; $R^7$ is (D)Phe, pCl(D)Phe, pNH$_2$Phe or (D)Tyr; $R^8$ is (D) or (L)Trp; $R^{11}$ is Phe, Gly or Ala; $R^{12}$ is Thr, Val, Ala, β-Ala, (L)2-Nal or (D)2-Nal; and $Y^1$ is selected from the group consisting of amide, thioether, thioester and disulfide (SEQ ID NO:2).

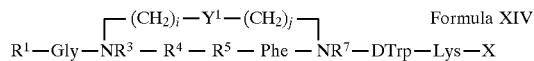

wherein i and j are independently 1 to 5; X designates a carboxy terminal amide or alcohol; $R^1$ is Ala or (D)2-Nal; $R^3$ is Phe, Gly, Ala or Lys; $R^4$ is Lys or Arg; $R^5$ is (L)Asn or (D)Asn; R6 is Phe, Gly, Ala or Lys; $R^7$ is Phe, Gly, Ala or Lys, and $Y^1$ is selected from the group consisting of amide, thioether, thioester and disulfide.

Another aspect of the present invention is a method for the preparation of cyclic peptides of the general Formula (I):

Formula (I)

wherein: a–c each independently designates an integer from 1 to 8 or zero; (AA) designates an amino acid residue wherein the amino acid residues in each chain may be the same or different; Q represents H or an acyl group; E represents a hydroxyl group, a carboxyl protecting group or an amino group, or the terminal carboxyl group can be reduced to $CH_2$—OH; $R^1$ to $R^4$ each designates an amino acid side-chain optionally bound with a specific protecting group; and the lines designate a bridging group of the Formula:

(i) —X—M—Y—W—Z—; or (ii) —X—M—Z— wherein M and W are independently selected from the group consisting of amide, thioether, thioester and disulfide; and X, Y and Z are each independently selected from the group consisting of alkylene, substituted alkylene, arylene, homo- or hetero-cycloalkylene and substituted cycloalkylene.

This method comprises the steps of incorporating at least one Nα-ω-functionalized derivative of amino acids of Formula (III):

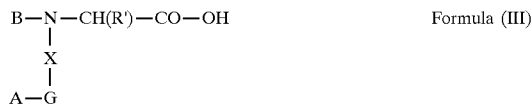

Formula (III)

wherein X is a spacer group selected from the group consisting of alkylene, substituted alkylene, arylene, cycloalkylene and substituted cycloalkylene; $R^1$ is an amino acid side chain, optionally bound with a specific protecting group; B is a protecting group selected from the group consisting of alkyloxy, substituted alkyloxy, or aryl carbonyls; and G is a functional group selected from the group consisting of amines, thiols, alcohols, carboxylic acids and esters, aldehydes, alcohols and alkyl halides; and A is a specific protecting group of G; into a peptide sequence and subsequently selectively cyclizing the functional group with one of the side chains of the amino acids in said peptide sequence or with another ω-functionalized amino acid derivative.

Preferred building units are the co-functionalized amino acid derivatives wherein X is alkylene; G is a thiol group, an amine group or a carboxyl group; R is phenyl, methyl or isobutyl; with the proviso that when G is an amine group, R is other than H.

Further preferred are ω-functionalized amino acid derivatives wherein R is protected with a specific protecting group.

More preferred are ω-functionalized amino acid derivatives of Formula III, wherein C is an amino group, a carboxyl group, or a thiol group:

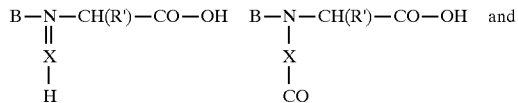

-continued

B—N—CH(R')—CO—OH
|
X
|
S wherein X, R, A and B are as defined above.

A further aspect of this invention is to provide methods for the preparation of novel backbone cyclic somatostatin analogs, comprising the steps of incorporating at least one Nα-ω-functionalized derivative of an amino acid into a peptide sequence and subsequently selectively cyclizing the functional group with one of the side chains of the amino acids in said peptide sequence, or with another ω-functionalized amino acid derivative. Backbone cyclized analogs of the present invention may be used as pharmaceutical compositions and for methods for the treatment of disorders including: post-surgical pain, all types of inflammation, in particular pancreatitis, cancers, endocrine disorders and gastrointestinal disorders.

Therefore, further objects of the present invention are directed to pharmaceutical compositions comprising pharmacologically active backbone cyclized peptide agonists and antagonists prepared according to the methods disclosed herein and a pharmaceutically acceptable carrier or diluent; and methods for the treatment of inflammation, cancer or endocrine disorders and gastrointestinal disorders therewith.

DETAILED DESCRIPTION OF THE INVENTION

Figure 1:
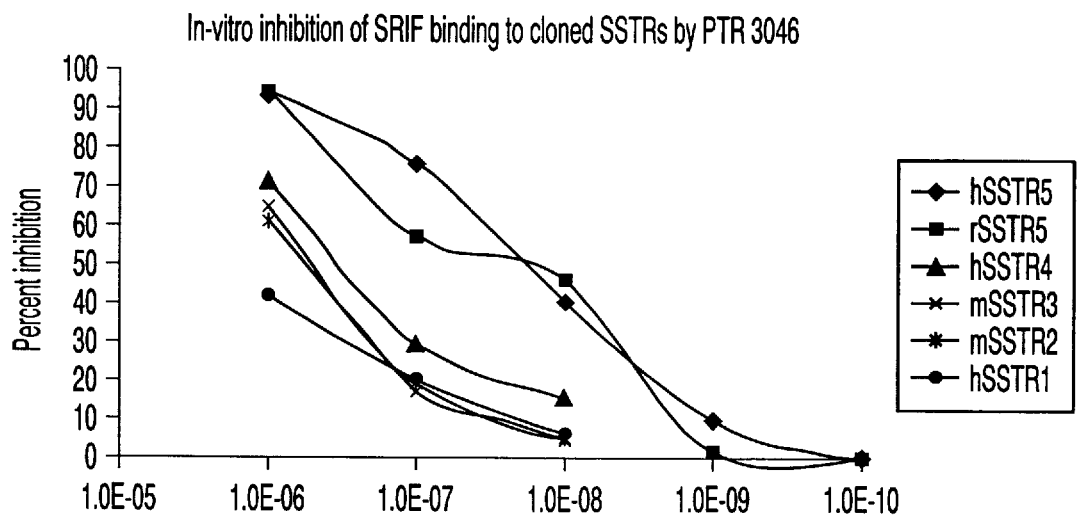
FIG. 1 is a graph showing the inhibition of somatostatin (SRIF-14) binding to the different SSTR subtypes, as a function of the concentration of the backbone cyclic somatostatin analog PTR 3046.

The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

By "stable compound" or "stable structure" is meant herein a compound that is sufficiently robust to survive isolation to a useful degree of purity from a reaction mixture, and formulation into an efficacious therapeutic agent.

As used herein and in the claims, "alkyl" or "alkylenyl" is intended to include both branched and straight-chain saturated aliphatic hydrocarbon groups having one to ten carbon atoms; "alkenyl" is intended to include hydrocarbon chains of either a straight or branched configuration having two to ten carbon atoms and one or more unsaturated carbon-carbon bonds which may occur in any stable point along the chain, such as ethenyl, propenyl, and the like; and "alkynyl" is intended to include hydrocarbon chains of either a straight or branched configuration having from two to ten carbon atoms and one or more triple carbon-carbon bonds which may occur in any stable point along the chain, such as ethynyl, propynyl, and the like.

As used herein and in the claims, "aryl" is intended to mean any stable 5- to 7-membered monocyclic or bicyclic or 7- to 14-membered bicyclic or tricyclic carbon ring, any of which may be saturated, partially unsaturated or aromatic, for example, phenyl, naphthyl, indanyl, or tetrahydronaphthyl tetralin, etc.

As used herein and in the claims, "alkyl halide" is intended to include both branched and straight-chain saturated aliphatic hydrocarbon groups having the one to ten carbon atoms, wherein 1 to 3 hydrogen atoms have been replaced by a halogen atom such as Cl, F, Br, and I.

As used herein and in the claims, the phrase "therapeutically effective amount" means that amount of novel backbone cyclized peptide analog or composition comprising same to administer to a host to achieve the desired results for the indications described herein, such as but not limited of inflammation, cancer, endocrine disorders and gastrointestinal disorders.

The term, "substituted" as used herein and in the claims, means that any one or more hydrogen atoms on the designated atom is replaced with a selection from the indicated group, provided that the designated atom's normal valency is not exceeded, and that the substitution results in a stable compound.

When any variable (for example R, X, Z, etc.) occurs more than one time in any constituent or in any Formula herein, its definition on each occurrence is independent of its definition at every other occurrence. Also, combinations of substituents and/or variables are permissible only if such combinations result in stable compounds.

As used herein "peptide" indicates a sequence of amino acids linked by peptide bonds. The somatostatin peptide analogs of this invention comprise a sequence of amino acids of 4 to 24 amino acid residues, preferably 6 to 14 residues, each residue being characterized by having an amino and a carboxy terminus.

A "building unit" indicates an NO derivatized a amino acid of the general Formula IV:

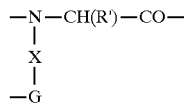

Formula (IV)

wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides; which is incorporated into the peptide sequence and subsequently selectively cyclized via the functional group G with one of the side chains of the amino acids in said peptide sequence or with another ω-functionalized amino acid derivative.

The methodology for producing the building units is described in international patent application PCT/IB95/ 00455, which is incorporated in its entirety by way of reference. The building units are abbreviated by the three letter code of the corresponding modified amino acid followed by the type of reactive group (N for amine, C for carboxyl), and an indication of the number of spacing methylene groups. For example, Gly-C2 describes a modified Gly residue with a carboxyl reactive group and a two carbon methylene spacer, and Phe-N3 designates a modified phenylalanine group with an amino reactive group and a three carbon methylene spacer.

As used herein "linear peptide" denotes the peptide sequence that is constructed only of amino acid residues and is devoid of any building units.

As used herein "backbone cyclic peptide" denotes an analog of a linear peptide which contains at least one building unit that has been liked to form a bridge via the alpha nitrogen of the peptide backbone to another building unit, or to another amino acid in the sequence. As used herein "pre-cyclic peptide" denotes an analog identical to the cyclic analog except that it is retained in the non-cyclized form to serve as control during the biological or other screening assays. The term non-cyclic can be used interchangeably with the term pre-cyclic. Certain abbreviations are used herein to describe this invention and the manner of making and using it. For instance, AcOH refers to acetic acid, Ada refers to adamantanacetyl, Adac refers to adamantanecarbonyl, Alloc refer to allyloxycarbonyl, Boc refers to the t-butyloxycarbonyl radical, BOP refers to benzotriazol-1-yloxy-tris-(dimethylamino)phosphonium hexafluorophosphate, BSA refers to bovine serum albumin, Cbz refers to the carbobenzyloxy radical, DCC refers to dicyclohexylcarbodiimide, DCM refers to Dichloromethane, Dde refers to 1-(4,4-dimethyl2,6-dioxocyclohex-1-ylidene-ethyl), DIEA refers to diisopropylethyl amine, DMF refers to dimethyl formamide, DPPA refers to diphenylphosphoryl azide, Dtc refers to 5,5-dimethylthiazolidine-4-carboxylic acid, EDC refers to N-ethyl-N' (dimethylaminopropyl)-carbodiimide, EDT refers to ethanedithiol, Fmoc refers to the fluorenylmethoxycarbonyl radical, GPI refers to guinea pig ileum, HATU refers to [O-(7-azabenzotriazol-1-yl)-1,1,3,3-tetramethyl uronium hexafluorophosphate, HBTU refers to 1-hydroxybenztriazolyltetramethyl-uronium hexafluorophosphate, HF refers to hydrofluoric acid, HOBT refers to 1-hydroxybenzotriazole, HPLC refers to high pressure liquid chromatography, MALDI-TOF MS refers to matrix-assisted laser desorption, time-of-flight mass spectrometry, Mts refers to the 4-methoxy-2,3,6-trimethylbenzenzsulfonyl, NBT refers to nitro blue tetrazolium, NMM refers to N-methylmorpholine, NMP refers to 1-methyl-2-pyrolidonone, PBS refers to phosphate buffered saline, Pmc refers to pentamethylchroman-6-sulfonyl, PNPP refers to p-nitrophenyl phosphate, PPA refers to 1-propanephosphoric acid cyclic anhydride, PyBOP refers to Benzotriazole-1-yl-oxy-tris-pyrrolidino-phosphonium hexafluorophosphate, PyBrOP refers to Bromo-tris-pyrrolidino-phosphonium hexafluorophosphate, RT refers to room temperature, SMPS refers to simultaneous multiple peptide synthesis, SRIF refers to Somatotropin Release Inhibitory Factor, TBTU refers to 2-(1H-benzotriazole-1-yl)-1,1,3,3-tetramethyluronium tetrafluoroborate, t-Bu refers to the tertiary butyl radical, TFA refers to trifluoroacetic acid, TIS refers to triisopropylsilane, Tpr refers to thiazolidine-4-carboxylic acid, Trt refers to trityl, Ts refers to toluenesulfonyl.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation. List of Non-coded amino acids: Abu refers to 2-aminobutyric acid, Aib refers to 2-amino-isobutyric acid, Cha refers to cyclohexylalanine, Hcys refer to homocystein, Hyp refers to S-trans-4-hydroxyproline, 1Nal refers to 1-naphthylalanine, 2Nal refers to 2-naphthylalanine, Nva refers to norvaline, Oic refers to octahydroindolecarboxylic acid, Phg refers to phenylglycine, pClPhe refers to p-chloro-phenylalanine, pFPhe refers to p-fluoro-phenylalanine, pNO$_2$Phe refers to p-nitro-phenylalanine, Thi refers to thienylalanine.

Synthetic Approaches

According to the present invention peptide analogs are cyclized via bridging groups attached to the alpha nitrogens of amino acids that permit novel non-peptidic linkages. In general, the procedures utilized to construct such peptide analogs from their building units rely on the known principles of peptide synthesis; most conveniently, the procedures can be performed according to the known principles of solid phase peptide synthesis. The innovation requires replacement of one or more of the amino acids in a peptide sequence by novel building units of the general Formula:

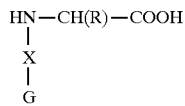

wherein R is the side chain of an amino acid, X is a spacer group and G is the functional end group by means of which cyclization will be effected. The side chain R is the side chain of any natural or synthetic amino acid that is selected to be incorporated into the peptide sequence of choice. X is a spacer group that is selected to provide a greater or lesser degree of flexibility in order to achieve the appropriate conformational constraints of the peptide analog. Such spacer groups include alkylene chains, substituted, branched and unsaturated alkylenes, arylenes, cycloalkylenes, and unsaturated and substituted cycloalkylenes. Furthermore, X and R can be combined to form a heterocyclic structure.

A preferred embodiment of the present invention utilizes alkylene chains containing from two to ten carbon atoms. The terminal (ω) functional groups to be used for cyclization of the peptide analog include but are not limited to:

a. Amines, for reaction with electrophiles such as activated carboxyl groups, aldehydes and ketones (with or without subsequent reduction), and alkyl or substituted alkyl halides.

b. Alcohols, for reaction with electrophiles such as activated carboxyl groups.

c. Thiols, for the formation of disulfide bonds and reaction with electrophiles such as activated carboxyl groups, and alkyl or substituted alkyl halides.

d. 1,2 and 1,3 Diols, for the formation of acetals and ketals.

e. Alkynes or Substituted Alkynes, for reaction with nucleophiles such as amines, thiols or carbanions; free radicals; electrophiles such as aldehydes and ketones, and alkyl or substituted alkyl halides; or organometallic complexes.

f. Carboxylic Acids and Esters, for reaction with nucleophiles (with or without prior activation), such as amines, alcohols, and thiols.

g. Alkyl or Substituted Alkyl Halides or Esters, for reaction with nucleophiles such as amines, alcohols, thiols, and carbanions (from active methylene groups such as acetoacetates or malonates); and formation of free radicals for subsequent reaction with alkenes or substituted alkenes, and alkynes or substituted alkynes.

h. Alkyl or Aryl Aldehydes and Ketones for reaction with nucleophiles such as amines (with or without subsequent reduction), carbanions (from active methylene groups such as acetoacetates or malonates), diols (for the formation of acetals and ketals).

i. Alkenes or Substituted Alkenes, for reaction with nucleophiles such as amines, thiols, carbanions, free radicals, or organometallic complexes.

j. Active Methylene Groups, such as malonate esters, acetoacetate esters, and others for reaction with electrophiles such as aldehydes and ketones, alkyl or substituted alkyl halides.

It will be appreciated that during synthesis of the peptide these reactive end groups, as well as any reactive side chains, must be protected by suitable protecting groups.

Suitable protecting groups for amines are alkyloxy, substituted alkyloxy, and aryloxy carbonyls including, but not limited to, tert butyloxycarbonyl (Boc), Fluorenylmethyloxycarbonyl (Fmoc), Allyloxycarbonyl (Alloc) and Benzyloxycarbonyl (Z).

Carboxylic end groups for cyclizations may be protected as their alkyl or substituted alkyl esters or thio esters or aryl or substituted aryl esters or thio esters. Examples include but are not limited to tertiary butyl ester, allyl ester, benzyl ester, 2-(trimethylsilyl)ethyl ester and 9-methyl fluorenyl.

Thiol groups for cyclizations may be protected as their alkyl or substituted alkyl thio ethers or disulfides or aryl or substituted aryl thio ethers or disulfides. Examples of such groups include but are not limited to tertiary butyl, trityl (triphenylmethyl), benzyl, 2-(trimethylsilyl)ethyl, pixyl(9-phenylxanthen-9-yl), acetamidomethyl, carboxymethyl, 2-thio-4-nitropyridyl.

It will further be appreciated by the artisan that the various reactive moieties will be protected by different protecting groups to allow their selective removal. Thus, a particular amino acid will be coupled to its neighbor in the peptide sequence when the $N^\alpha$ is protected by, for instance, protecting group A. If an amine is to be used as an end group for cyclization in the reaction scheme the $N^\omega$ will be protected by protecting group B, or an ε amino group of any lysine in the sequence will be protected by protecting group C, and so on.

The coupling of the amino acids to one another is performed as a series of reactions as is known in the art of peptide synthesis. Novel building units of the invention, namely the $N^\alpha$-ω functionalized amino acid derivatives are incorporated into the peptide sequence to replace one or more of the amino acids. If only one such $N^\alpha$-ω functionalized amino acid derivative is selected, it will be cyclized to a side chain of another amino acid in the sequence. For instance: (a) an $N^\alpha$-(ω-amino alkylene) amino acid can be linked to the carboxyl group of an aspartic or glutamic acid residue; (b) an $N^\alpha$-(ω-carboxylic alkylene) amino acid can be linked to the ε-amino group of a lysine residue; (c) an $N^\alpha$-(ω-thio alkylene) amino acid can be linked to the thiol group of a cysteine residue; and so on. A more preferred embodiment of the invention incorporates two such $N^\alpha$-ω-functionalized amino acid derivatives which may be linked to one another to form N-backbone to N-backbone cyclic peptide analogs. Three or more such building units can be incorporated into a peptide sequence to create bi-cyclic peptide analogs as will be elaborated below. Thus, peptide analogs can be constructed with two or more cyclizations, including N-backbone to N-backbone, as well as backbone to side-chain or any other peptide cyclization.

As stated above, the procedures utilized to construct somatostatin analogs of the present invention from novel building units generally rely on the known principles of peptide synthesis. However, it will be appreciated that accommodation of the procedures to the bulkier building units of the present invention may be required. Coupling of the amino acids in solid phase peptide chemistry can be achieved by means of a coupling agent such as but not limited to: dicyclohexycarbodiimide (DCC), bis(2-oxo-3oxazolidinyl) phosphinic chloride (BOP-Cl), benzotriazolyl-N-oxytrisdimethyl-aminophosphonium hexafluoro phosphate (BOP), 1-oxo-1-chlorophospholane (Cpt-Cl), hydroxybenzotriazole (HOBT), or mixtures thereof.

It has now been found that coupling of the subsequent amino acid to the bulky building units of the present invention may require the use of additional coupling reagents including, but not limited to: coupling reagents such as PYBOP® (Benzotriazole-1-yl-oxy-tris-pyrrolidino-phosphonium hexafluorophosphate), PyBrOP® (Bromo-tris-pyrrolidino-phosphonium hexafluorophosphate), HBTU (2-(1H-Benzotriazole-1-yl)-1,1,3,3-tetramethyluronium hexafluoro-phosphate), TBTU (2-(1H-Benzotriazole-1-yl)-1,1,3,3-tetramethyluronium tetrafluoroborate).

Novel coupling chemistries may be used, such as pre-formed urethane-protected N-carboxy anhydrides (UNCA'S) and pre-formed acyl halides most preferably acy chlorides. Such coupling may take place at room temperature and also at elevated temperatures, in solvents such as toluene, DCM (dichloromethane), DMF (dimethylformamide), DMA (dimethylacetamide), NMP (N-methyl pyrrolidinone) or mixtures of the above.

One object of the present invention is a method for the preparation of backbone cyclized somatostatin analogs of general Formula (I):

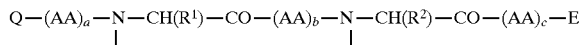

Formula (I)

wherein the substituents are as defined above;

comprising the steps of incorporating at least two $N^\alpha$-$\omega$-functionalized derivatives of amino acids of Formula (III):

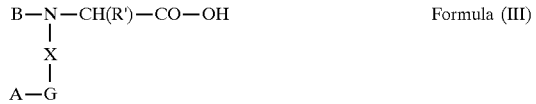

Formula (III)

wherein X is a spacer group selected from the group consisting of alkylene, substituted alkylene, arylene, cycloalkylene and substituted cycloalkylene; R' is an amino acid side chain such as H, $CH_3$ etc., optionally bound with a specific protecting group; B is a protecting group selected from the group consisting of alkyloxy, substituted alkyloxy, or aryloxy carbonyls; and G is a functional group selected from the group consisting of amines, thiols, alcohols, carboxylic acids and esters, aldehydes, alcohols and alkyl halides; and A is a specific protecting group of G;

into an amino acid sequence to yield a compound of Formula:

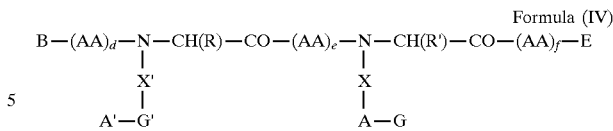

Formula (IV)

(ii) selectively removing protecting groups A and A' and reacting the terminal groups G and G' to form a compound of the Formula:

Formula (I)

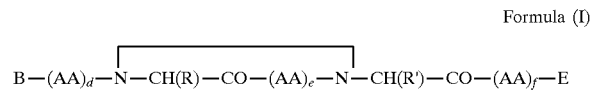

wherein d, e and f are independently an integer from 1 to 10; (AA) is an amino acid residue wherein the amino acid residues in each chain may be the same or different; E is an hydroxyl group, a carboxyl protecting group or an amino group; R and R' are independently an amino acid side-chain such as H, $CH_3$, etc.; and the line designates a bridging group of the Formula:
—X—M—Y—W—Z— wherein M and W are independently selected from the group consisting of disulfide, amide, thioether, imine, ether, and alkene; X, Y and Z are independently selected from the group consisting of alkylene, substituted alkylene, arylene, cycloalkylene, and substituted cycloalkylene;

(iii) removing all remaining protecting groups to yield a compound of Formula (Ia).

Bicyclic analogs are prepared in the same manner, that is, by repetition of steps (ii) and (iii). The determination of which residues are cyclized with which other residues is made through the choice of blocking groups. The various blocking groups may be removed selectively, thereby exposing the selected reactive groups for cyclization.

Preferred are methods for the preparation of backbone cyclized peptide analogs of Formula (I) wherein G is an amine, thiol or carboxyl group; R and $R^1$ are each other than H, such as $CH_3$, $(CH_3)_2CH$—, $(CH_3)_2CHCH_2$—, $CH_3CH_2CH(CH_3)$—, $CH_3S(CH_2)_2$—, $HOCH_2$—, $CH_3CH(OH)$—, $HSCH_2$—, $NH_2C(=O)CH_2$—, $NH_2C(=O)(CH_2)_2$—, $HOC(=O)CH_2$—, $HOC(=O)(CH_2)_2$—, $NH_2(CH_2)_4$—, $C(NH_2)_2NH(CH_2)_3$—, HO—phenyl—$CH_2$—, benzyl, methylindole, and methylimidazole, and wherein E is covalently bound to an insoluble polymeric support.

Another object of the present invention is a method for the preparation of backbone cyclized peptide analogs of Formula (II):

Formula (II)

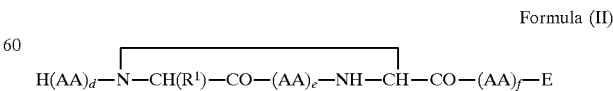

wherein the substituents are as defined above;

comprising the steps of: incorporating at least one $\omega$-functionalized amino acid derivative of the general Formula (III):

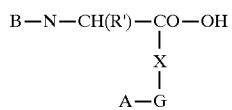

Formula (III)

wherein X is a spacer group selected from the group consisting of alkylene, substituted alkylene, arylene, cycloalkylene and substituted cycloalkylene; R is the side chain of an amino acid, such as H, CH$_3$, etc.; B is a protecting group selected from the group consisting of alkyloxy, substituted alkyloxy, or aryloxy carbonyls; and G is a functional group selected from the group consisting of amines, thiols, alcohols, carboxylic acids and esters or alkyl halides; and A is a protecting group thereof; into a peptide sequence and subsequently selectively cyclizing the functional group with one of the side chains of the amino acids in said peptide sequence.

Preferred is the method for the preparation of backbone cyclized peptide analogs of Formula (II) wherein G is a carboxyl group or a thiol group; R is CH$_3$ (CH$_3$)$_2$CH—, (CH$_3$)$_2$CHCH$_2$—, CH$_3$CH$_2$CH(CH$_3$)—, CH$_3$S(CH$_2$)$_2$—, HOCH$_2$—, CH$_3$CH(OH)—, HSCH$_2$—, NH$_2$C(=O)CH$_2$—, NH$_2$C(=O)(CH$_2$)$_2$—, HOC(=O)CH$_2$—, HOC(=O)(CH$_2$)$_2$—, NH$_2$(CH$_2$)$_4$—, C(NH$_2$)$_2$NH(CH$_2$)$_3$—, HO—phenyl—CH$_2$—, benzyl, methylindole, and methylimidazole, and wherein E is covalently bound to an insoluble polymeric support.

Preparation of Peptides with Backbone to Side Chain Cyclization.

One preferred procedure for preparing the desired backbone cyclic peptides involves the stepwise synthesis of the linear peptides on a solid support and the backbone cyclization of the peptide either on the solid support or after removal from the support. The C-terminal amino acid is bound covalently to an insoluble polymeric support by a carboxylic acid ester or other linkages such as amides. An example of such support is a polystyrene-co-divinyl benzene resin. The polymeric supports used are those compatible with such chemistries as Fmoc and Boc and include for example PAM resin, HMP resin and chloromethylated resin. The resin bound amino acid is deprotected for example with TFA and to it is coupled the second amino acid, protected on the N$^\alpha$ for example by Fmoc, using a coupling reagent like BOP. The second amino acid is deprotected using for example piperidine 20% in DMF. The subsequent protected amino acids can then be coupled and deprotected at ambient temperature. After several cycles of coupling and deprotection that gives peptide, an amino acid having for example carboxy side chain is coupled to the desired peptide. One such amino acid is Fmoc-aspartic acid t-butyl ester. After deprotection of the N$^\alpha$ Fmoc protecting group, the peptide is again elongated by methods well known in the art. After deprotection a building unit for backbone cyclization is coupled to the peptide resin using for example the coupling reagent BOP. One such building unit is for example Fmoc-N$^\alpha$-(ω-Boc-amino alkylene)amino acid. After deprotection the peptide can then be elongated, to the desired length using methods well known in the art. The coupling of the protected amino acid subsequent to the building unit is performed by such coupling agents exemplified by PyBrOP to ensure high yield. After the linear, resin bound peptide, has been prepared the co-alkylene-protecting groups, for example Boc and t-Bu, are removed by mild acid such as TFA. The resin bound peptide is then divided into several parts. One part is subjected to on-resin cyclization using for example TBTU as cyclization agent in DMF to ensure high yield of cyclization, to give the N-backbone to side chain cyclic peptide resin. After cyclization on the resin the terminal amino protecting group is removed by agents such as piperidine and the backbone to side chain cyclic peptide is obtained after treatment with strong acid such as HF. Alternatively, prior to the removal of the backbone cyclic peptide from the resin, the terminal amino group is blocked by acylation with agents such as acetic anhydride, benzoic anhydride or any other acid such as adamantyl carboxylic acid activated by coupling agents such as BOP.

The other part of the peptide-resin undergoes protecting of the side chains used for cyclization, for example the ω-amino and carboxy groups. This is done by reacting the ω-amino group with for example Ac$_2$O and DMAP in DMF and activating the free ω-carboxy group by, for example, DIC and HOBT to give the active ester which is then reacted with, for example, CH$_3$NH$_2$ to give the non-cyclic analog of the cyclic peptide. Removal of the peptide from the resin and subsequent removal of the side chains protecting groups by strong acid such as HF to gives the non-cyclic analog of the backbone to side chain cyclic peptide.

The linear and/or non-cyclic analogs are used as reference compounds for the biological activity of their corresponding cyclic compounds.

Synthetic Approach for Generation of Backbone Cyclized Somatostatin Libraries.

The general methodology for preparing the cyclic peptide libraries of this invention involves solid phase peptide synthesis using an orthogonal protection scheme which allows for chain elongation, selective removal of the protecting groups, cyclization of the protected peptides and removal of all side-chains protecting groups with or without cleavage from the resin. It is desirable that the various peptide sequences be present in the libraries in substantially equal amount.

The coupling reactions are performed by methods to create amide or ester bonds and are performed by methods familiar in the art as described herein. Typical coupling reagents are carbodiimides, activated anhydrides and esters and acyl halides. Reagents such as EDC, DCC, DPPA, PPA, BOP, PyBOP, PyBrop, HATU, HBTU, TBTU, HOBT and N-hydroxysuccinimide are typical.

After completion of the solid phase peptide elongation, by any scheme, portions of the peptide are cyclized via the bridging groups attached to the backbone amine bond nitrogens of the building units. It is preferable that a portion is retained in the non-cyclized form to serve as control during the biological or other screening assays. This portion of the peptide analog library, which contains the building units identical to those of the backbone cyclized library, but is devoid of the conformational constraint of the latter, is referred to as the "pre-cyclic". Alternatively, in any of the synthesis schemes, the backbone cyclization step may be performed and additional coupling cycles of amino acid residues may then be carried out.

Portions of the peptide may be cleaved from the resin and protecting groups removed, as required prior to assay of biological activity. The peptides are cleaved from the resin support by methods known in the art, the precise method being dependent upon the characteristics of the resin. It will be understood by those skilled in the art that the removal of certain protecting groups may occur simultaneously with cleavage of the peptide from the resin.

Typically the coupling between the resin and the first amino acid will form an ester bond, which will yield a carboxylic acid group on the peptide when it is cleaved from the resin. HMPB, Rink, PAM, Hycram and hydroxymethyl resins are exemplary. In addition, the carboxy terminal amino acid group may be converted to an amide, an ester or reduced to a terminal alcohol.

The reactive functional groups of the side chains of each amino acid or peptide are suitably protected as known in the peptide art. For example, the Boc, Cbz or Fmoc group may be used for protection of an amino group, especially an α-amino group. An alkyl (e.g., t-Bu, Me), cHex, benzyl or allyl ester may be used for the protection of the side chain carboxyl of Asp or Glu. A benzyl, or suitably substituted benzyl, trityl, Alloc or T-Bu group is used to protect the mercapto group of cysteine, or other thiol containing residues; or the hydroxyl of Tyr, Ser or Thr. Cys and other sulfur-containing amino acids may also be protected by the Acm group or by formation of a disulfide with a thioalkyl (e.g., ethyl mercaptan) or thioaryl group. The benzyl/ benzyloxymethyl, or a suitably substituted benzyl/ benzyloxymethyl, Boc or formyl group may be used for protection of the imidazolyl group of His; and the Pmc, nitro, or a suitably substituted benzene-sulfonyl group (e.g., Ts, Mts) for protection of the guanidino nitrogen or Arg. The phthalamido, Boc, Fmoc, Alloc carbobenzyloxy or benzyl group, or suitably substituted benzyl or benzyloxy group, may be used for protecting the ε-amino group of lysine. Suitable substitution of the carbobenzyloxy or benzyl protecting groups is substitution with one to five chloro, bromo, nitro, methoxy or methyl groups, usually ortho and/or para, and is used to modify the reactivity of the protective group. These protective groups are removed by such methods as catalytic hydrogenation, sodium in liquid ammonia, hydrazine, base, TFA or HF treatment, as known in the art. The choice of side chain protecting groups is chosen so that they will not be removed under conditions which are used to deprotect the reactive functional group used in the coupling reaction (e.g., generally the α-amino group) to form the peptide backbone of the peptide chain. The protective group of the reactive functional group is removed prior to coupling each successive amino acid.

The bridging groups of the building units (i.e., G in Formula IV) are used according to the present invention with an orthogonal protection scheme, such that these protecting groups can be removed selectively, under conditions which do not affect the protecting groups on the side chains or cleavage of the peptide from the resin. This enables backbone cyclization on the resin, which is preferred synthetically. Alternatively, the fully protected peptide may be removed from the resin, and cyclization performed in solution after selective removal of the protecting groups of the building units.

The cyclization reaction is carried out by means of selectively coupling the bridging group of one building unit to a bridging group of another building unit or amino acid side chain. By way of example, PyBOP is a particularly useful reagent for conducting the coupling reaction, in case of formation of an amide bond. To form a disulfide bridge oxidative conditions are used.

In a most preferred embodiment according to the present invention, the amino acid sequence scaffold is based on known active sequences from natural or synthetic peptides having somatostatin activity. It will thus be possible to further improve the activity of such known sequences upon rigidification of the active conformer.

Amino acids in certain positions are replaced by Backbone-Cyclization Building-Units or by natural and nonnatural trifunctional amino acids such as Asp, Glu, Cys, Hcys, Lys, Orn and their D counterparts. Thus positional as well as structural scans are performed by changing the position of cyclization, the link of the ring to the backbone, the chirality at the position of cyclization, the ring forming bond, the ring size and the exact placement of the bond within the ring. These variations may also be performed in conjunction with changing the amino acid sequence of the peptide.

General synthesis of libraries of somatostatin analogs.

To determine the optimum compounds, a library of differently constrained analogs is generated and then screened. The libraries were synthesized on TentaGel amide Resin (substitution level of 0.2–0.3 mmol/g) using conventional solid-phase peptide synthesis (known to those skilled in the art). In most cases NMP was used as a solvent, DMF in few cases. Synthesis scale was 0.2–2 μmole for each peptide in library or sub-library. Unless otherwise mentioned, all reactions were performed at room temperature.

In each coupling step where more than one amino acid had to be coupled, the resin was divided into the appropriate number of portions and different amino acid was added to each portion. Coupling was performed, twice for each position with 3 molar excess of each amino acid, 3 molar excess of PyBrop and 6 molar excess of DIEA for duration of 1–16 hours. All amino acids were protected with FMOC in their α-amine. Side-chain protections were as follow: His(Trt); Lys(Boc or Dde); Orn(Boc); Ser(tBu); Thr(tBu); Tyr(tBu).

After double coupling, the resin portions were washed, recombined and FMOC deprotection was performed using 20% piperidine in NMP for total of 20–40 minutes. After additional washes the resin was divided again (if necessary) for the coupling of the next amino acid/s.

Before cyclization, the Allyl/Alloc protection of the amine and carboxyl of the building units were removed by treatment with a solution of 2 mole equivalents (one for each Allyl/Alloc molecule in peptide), of Pd(PPh3)$_4$ dissolved in chloroform containing 2.5% AcOH and 5% NMM for 2–2.5 hours or twice for 1 hour, resins were washed with the above solvent without the palladium before and after treatment, additional washes with NMP were made at the end of the removal process.

The peptides were cleaved from the resin portions after washes with DCM, by double treatment with TFA 70%, H$_2$O 5%, TIS 1%, EDT 2.5%, DCM (mixture A) or TFA 70%, H$_2$O 5%, TIS 1%, Phenol 5%, DCM (mixture B) or 60% TFA, 10% H$_2$O and 30% DCM (mixture C) plus additional wash with neat TFA. The three cleavage solutions of each resin portion were collected together, evaporated with nitrogen stream, 0.5–1 ml of H$_2$O were added to each sample that was then freeze-dried. The peptide mixtures were then partially purified on C-18 SEP-PAK (Millipore Corp.) using 0.1% acetic acid or TFA in H$_2$O as buffer A and 50–80% CH$_3$CN in 0.1% acetic acid/H$_2$O as buffer B and freeze-dried.

Each sub-library synthesized is characterized by mass spectrometry (MALDI-TOF MS), and amino acid analysis.

The building units are abbreviated by the three letter code of the corresponding modified amino acid followed by the type of reactive group (N for amine, C for carboxyl), and an indication of the number of spacing methylene groups. For example, Gly-C2 describes a modified Gly residue with a carboxy reactive group and a two carbon methylene spacer, and Phe-N3 designates a modified phenylalanine group with a amino reactive group and three carbon methylene spacer.

General screening of somatostatin analogs

Somatostatin analogs synthesized are typically tested in vitro for their inhibition of the natural peptide (SRIF-14) binding to its 7-transmembranal receptors, and for their influence on second messengers and cell growth; and in vivo for inhibition of hormones and enzyme secretion.

The analogs are further tested in vitro for their influence on cyclic adenosine monophosphate (cAMP) levels, tyrosine phosphatase activity, growth hormone secretion, and cell growth. The libraries are further tested in vivo for the inhibition of growth-hormone release, and amylase, gastric acid, insulin and glucagon secretion in animals.

Metabolic stability tests as parameter for selection:

Analogs are tested for stability by their resistance to enzymatic degradation by incubation in serum or in tissue homogenate, separation of the proteins and recording of the peptide peaks by HPLC before and after incubation. The peptide peaks that are not changed with increased incubation time are most stable. These peaks are separated and characterized by mass spectrometry, N-terminal sequence and comparison to purified peptide peaks. In this way the most stable peptides from library or sub-library are rapidly identified.

Conformationally constrained somatostatin analogs constructed based in part on the sequences of a number of known biologically active peptides or based on previously unknown novel sequences are presented in the examples below. The following examples are intended to illustrate how to make and use the compounds and methods of this invention and are in no way to be construed as a limitation.

EXAMPLES

Synthetic examples

Different series of somatostatin analogs were synthesized, either as individual backbone cyclized peptides or as libraries.

Three series of octapeptide somatostatin analogs corresponding to general Formula (Va) of the present invention were individually synthesized, characterized, and tested for biological activity.

1) The first series of compounds corresponds to the general Formula (Va), wherein $R^5$ is (D)Phe; $R^7$ is Phe; $R^{10}$ is Thr; and $R^{12}$ is Thr This series, therefore, comprises compounds of the specific formula:

H-(D)Phe-$R^6$-Phe-(D)Trp-Lys-Thr-$R^{11}$-Thr-NH$_2$ wherein $R^6$ and $R^{11}$ are $N^\alpha$ ω-functionalized alkylene amino acid building units.

2) The second series of compounds corresponds to the general Formula (Va), wherein $R^5$ is (D)Phe; $R^7$ is Phe; $R^{10}$ is absent; and $R^{12}$ is Thr. This series, therefore, comprises compounds of the specific formula:

H-(D)Phe-$R^6$-Phe-(D)Trp-Lys-$R^{11}$-Thr-NH$_2$
wherein $R^6$ and $R^{11}$ are $N^\alpha$ ω-functionalized alkylene amino acid building units.

3) The third series of compounds corresponds to the general Formula (Va), wherein $R^5$ is (D)Phe; and $R^7$ is Phe. This series, therefore, comprises compounds of the specific formula:

H-(D)Phe-$R^6$-Phe-(D)Trp-Lys-$R^{10}$-$R^{11}$-$R^{12}$-NH$_2$
wherein $R^6$ and $R^{11}$ are $N^\alpha$ ω-functionalized alkylene amino acid building units.

The structures of these novel synthetic peptide analogs into which $N^\alpha$ ω-functionalized amino acid building units were incorporated, are summarized in Tables 1, 2 and 3. In these three series, the building units used were glycine building units in which the bridging groups, attached via the alpha nitrogens to the peptide backbone, were varied.

For the sake of simplicity, these three series are referred to herein as the SST Gly$^6$, Gly$^{11}$; SST Gly$^6$, Gly$^{10}$; and SST Gly$^6$ Gly$^{11}$ $R^{10}$ $R^{12}$, respectively.

In each series, the position of the cyclization points was constant; in the first and second series the length and direction of the bridge was varied, whereas in the third series the bridge was constant and residues at positions 10 and 12 were varied. Thus, C2, N2 refers to a bridge consisting of an amide bond in which the carbonyl group is closer to the amino end of the peptide and which contains a two carbon methylene group between the bridge amide and each of the backbone nitrogens involved in the bridge.

Peptide assembly was carried out either manually or with an automatic peptide synthesizer (Applied Biosystems Model 433A). Following peptide assembly, de-protection of bridging groups that form the cyclization arms was carried out with Pd(PPh$_3$)$_4$ (palladium tetrakis triphenyl phosphine) in the case of Allyl/Alloc protecting groups or with TFA in the case of tBu/Boc protecting groups. For obtaining the non-cyclic analog, the peptides were cleaved from the resin at this stage. Cyclization of the peptides was carried out with PyBOP. Cleavage of the peptides from the polymeric support was carried out with suitable reagents depending on the type of resin used, e.g., with TFA for Rink amide type resins and with HF for mBHA (para-methyl benzhydryl amine) type resins. The crude products were characterized by analytical HPLC. The peptides were purified by preparative reversed phase HPLC. The purified products were characterized by analytical HPLC, mass spectroscopy, and amino acid analysis.

TABLE 1

SST Gly$^6$, Gly$^{11}$ analogs

| Example No. | Bridging Groups | Compound Number | Method | Crude Yield |
|---|---|---|---|---|
| 1 | C1,N2 Cyclic | DE-3-32-4 | 1 | NA** |
| 2 | C1,N2 Non-cyclic | DE-3-32-2 | 1 | NA |
| 3 | C1,N3 Cyclic | PTR 3004 | 2 | 79 mg |
| 4 | C1,N3 Non-cyclic | PTR 3005 | 2 | 34 mg |
| 5 | C2,N2 Cyclic | PTR 3002 | 1 | NA |
| 6 | C2,N2 Non-cyclic | PTR 3001 | 1 | NA |
| 7 | C2,N3 Cyclic | PTR 3007 | 2 | 40 mg |
| 8 | C2,N3 Non-cyclic | PTR 3008 | 2 | 40 mg |
| 9 | N2,C2 Cyclic | YD-9-166-1 | 2 | NA |
| 10 | N2,C2 Non-cyclic | YD-9-168-1 | 2 | NA |
| 11 | N3,C2 Cyclic | PTR 3010 | 2 | 100 mg |
| 12 | N3,C2 Non-cyclic | PTR 3011 | 2 | NA |
| 13 | Linear* | PTR 3003 | 3 | 96 mg |

*Linear refers to the identical sequence with underivatized Gly residues in place of $R^6$ and $R^{11}$.
**NA denotes not available.

Table 1 methods:

1) Manual synthesis on mBHA resin. HF cleavage.
2) Manual synthesis on Rapp TentaGel resin. TFA cleavage.
3) Rink amide resin; assembly in automated peptide synthesizer, 0.1 mmol scale.

TABLE 2

SST Gly$^6$, Gly$^{10}$ analogs

| Example No. | Bridging Groups | Compound Number | Method | Crude Yield |
|---|---|---|---|---|
| 14 | C1,N2 Cyclic | YD-9-171-3 | 1 | 20 mg |
| 15 | C1,N2 Non-cyclic | YD-9-171-2 | 1 | 10 mg |
| 16 | C1,N3 Cyclic | YD-9-175-3 | 1 | 44.9 mg |
| 17 | C1,N3 Non-cyclic | YD-9-175-2 | 1 | 25.4 mg |
| 18 | C2,N2 Cyclic | PTR 3019 | 1 | 40 mg |
| 19 | C2,N2 Non-cyclic | PTR 3020 | 1 | 26 mg |
| 20 | C2,N3 Cyclic | YD-5-28-3 | 3 | 101.5 mg |
| 21 | C2,N3 Non-cyclic | YD-5-28-2 | 3 | 48.3 mg |
| 22 | N2,C2 Cyclic | PTR 3016 | 2 | 60 mg |

TABLE 2-continued

SST Gly$^6$, Gly$^{10}$ analogs

| Example No. | Bridging Groups | Compound Number | Method | Crude Yield |
|---|---|---|---|---|
| 23 | N2,C2 Non-cyclic | PTR 3017 | 2 | 40 mg |
| 24 | N3,C2 Cyclic | YS-8-153-1 | 2 | 93 mg |
| 25 | N3,C2 Non-cyclic | YS-8-152-1 | 2 | 54 mg |
| 26 | *Linear | PTR 3021 | 1 | 100 mg |
| 27 | N3,C2 Cyclic** | PTR 3013 | | 67 mg |
| 28 | N3,C2 Non-cyclic** | PTR 3014 | | 48 mg |

*Linear refers to the identical sequence with Gly residues in place of R$^6$ and R$^{10}$.
**These analogs comprise of the same SST sequence in which the N terminal D-Phe$^5$ is absent and the N-terminus is acetylated.

Table 2 methods:
1) Assembly in automated peptide synthesizer, 0.1 mmol scale. (HBTU).
2) Manual synthesis; PyBrop.
3) Assembly in automated peptide synthesizer, 0.25 mmol scale. (HBTU).

TABLE 3

Somatostatin analogs based on: H—(D)Phe—R$^6$—Phe—(D)Trp—Lys—R$^{10}$—R$^{11}$—R$^{12}$—NH$_2$

| Example No. | Analog | R$^{10}$ | R$^{12}$ | Yield (mg) |
|---|---|---|---|---|
| 29 | GGP-22-65 | Nva | Thr | 390 |
| 30 | GGP-22-63 | Val | Thr | 300 |
| 31 | GGP-22-61 | Abu | Thr | 340 |
| 32 | GGP-22-59 | Ser | Thr | 350 |
| 33 | GGP-22-75 | Thr | Nal | 125 |
| 34 | GGP-22-81 | Val | Nal | 210 |
| 35 | GGP-22-82 | Abu | Nal | 200 |
| 36 | GGP-22-77 | Ser | Nal | 190 |
| 37 | GGP-22-83 | Thr | (D)Nal | 68 |
| 38 | GGP-22-89 | Val | (D)Nal | 58 |
| 39 | GGP-22-87 | Abu | (D)Nal | 65 |
| 40 | GGP-22-85 | Ser | (D)Nal | 58 |

Example 41. Detailed synthesis of SST Gly$^6$, Gly$^{10}$ N3,C2 analog

Five grams of Rink amide resin (NOVA) (0.49 mmol/g), were swelled in N-methylpyrrolidone (NMP) in a reaction vessel equipped with a sintered glass bottom and placed on a shaker. The Fmoc protecting group was removed from the resin by reaction with 20% piperidine in NMP (2 times 10 minutes, 25 ml each). Fmoc removal was monitored by ultraviolet absorption measurement at 290 nm. A coupling cycle was carried out with Fmoc-Thr(OtBu)-OH (3 equivalents) PyBrop (3 equivalents) DIEA (6 equivalents) in NMP (20 ml) for 2 hours at room temperature. Reaction completion was monitored by the qualitative ninhydrin test (Kaiser test). Following coupling, the peptide-resin was washed with NMP (7 times with 25 ml NMP, 2 minutes each). Capping was carried out by reaction of the peptide-resin with acetic anhydride (capping mixture: HOBt 400 mg, NMP 20 ml, acetic anhydride 10 ml, DIEA 4.4 ml) for 0.5 hours at room temperature. After capping, NMP washes were carried out as above (7 times, 2 minutes each). Fmoc removal was carried out as above. Fmoc-Phe-OH was coupled in the same manner, and the Fmoc group removed, as above. The peptide resin was reacted with Fmoc-Gly-C2 (Allyl) building unit: coupling conditions were as above. Fmoc removal was carried out as above. Fmoc-Lys(Boc)-OH was coupled to the peptide resin by reaction with HATU (3 equivalents) and DIEA (6 equivalents) at room temperature overnight and then at 50° for one hour. Additional DIEA was added during reaction to maintain a basic medium (as determined by pH paper to be about 9). This coupling was repeated. Coupling completion was monitored by the Fmoc test (a sample of the peptide resin was taken and weighed, the Fmoc was removed as above, and the ultraviolet absorption was measured). Fmoc-D-Trp-OH was couped to the peptide resin with PyBrop, as described above. Following Fmoc removal, Fmoc-Phe-OH was coupled in the same way. Synthesis was continued with one-fifth of the peptide resin.

Following Fmoc removal, the second building unit was introduced: Fmoc-Gly-N3(Alloc)-OH by reaction with PyBrOP, as described above. Capping was carried out as described above. Following Fmoc removal, the peptide-resin was divided into two equal portions. Synthesis was continued with one of these portions. Boc-D-Phe-OH was coupled by reaction with HATU, as described above for Fmoc-Lys(Boc)-OH. Capping was carried out as above.

The Allyl and Alloc protecting groups were removed by reaction with Pd(PPh$_3$)$_4$ and acetic acid 5%, morpholine 2.5% in chloroform, under argon, for 2 hours at room temperature. The peptide resin was washed with NMP as above. Two-thirds of the resin were taken for cyclization. Cyclization was carried out with PyBOP 3 equivalents, DIEA 6 equivalents, in NMP, at room temperature overnight. The peptide resin was washed and dried. The peptide was cleaved from the resin by reaction with TFA 81.5%, phenol 5%, water 5%, EDT 2.5%, TIS (tri-isopropyl-silane) 1%, and 5% methylene chloride, at 0° C. for 15 minutes and 2 hours at room temperature under argon. The mixture was filtered into cold ether (30 ml, 0° C.) and the resin was washed with a small volume of TFA. The filtrate was placed in a rotary evaporator and all the volatile components were removed. An oily product was obtained. It was triturated with ether and the ether decanted, three times. A white powder was obtained. This crude product was dried. The weight of the crude product was 93 mg.

Additional series of backbone cyclized somatostatin analogs were synthesized individually including the following:
1) heptapeptide series:

NPhe-Tyr-(D)Trp-Lys-Val-NPhe-Thr-NH$_2$ 2) heptapeptide series:

NPhe-Phe-(D)Trp-Lys-R$^{10}$-NPhe-R$^{12}$-NH$_2$

3) Heptapeptides series:

NPhe-Phe-Trp-Lys-Gly-NPhe-R$^{12}$-NH$_2$

In the first series (table 4), the length and direction of the bridge was varied, whereas in the second (table 5), and third (table 6), series the residues at positions 10 and/or 12 were varied.

TABLE 4

Heptapeptide somatostatin analogs based on:
R$^6$—Tyr—(D)Trp—Lys—val—R$^{11}$—Thr—NH$_2$

| Example No. | Analog | R$^6$ | R$^{11}$ | Yield (mg) |
|---|---|---|---|---|
| 42 | GGP-22-151 | Phe—N2 | Phe—C3 | 290 |
| 43 | GGP-22-135 | Phe—N3 | Phe—C3 | 25 |
| 44 | GGP-22-159a | Phe—N2 | Phe—C2 | 28 |
| 45 | GGP-22-159b | Phe—N3 | Phe—C2 | 30 |
| 46* | GGP-22-161a | Phe—C2 | Phe—N2 | 56 |
| 47 | GGP-22-161b | Phe—C3 | Phe—N2 | 65 |
| 48 | GGP-22-163a | Phe—C1 | Phe—N3 | 61 |

TABLE 4-continued

Heptapeptide somatostatin analogs based on:
$R^6$—Tyr—(D)Trp—Lys—val—$R^{11}$—Thr—$NH_2$

| Example No. | Analog | $R^6$ | $R^{11}$ | Yield (mg) |
|---|---|---|---|---|
| 49 | GGP-22-163b | Phe—C1 | Phe—N3 | 68 |
| 50 | GGP-22-163c | Phe—C3 | Phe—N3 | 10 |

*PTR-3046

TABLE 5

Additional heptapeptide somatostatin analogs based on: $R^6$—Phe—(D)Trp—Lys—$R^{10}$—$R^{11}$—$R^{12}$—$NH_2$

| Example No. | Analog | $R^6$ | $R^{10}$ | $R^{11}$ | $R^{12}$ | Yield (mg) |
|---|---|---|---|---|---|---|
| 51 | GGP-22-53 | Phe—N2 | Val | Phe—C3 | Val | 200 |
| 52 | GGP-22-55 | Phe—N2 | Val | Phe—C3 | Thr | 460 |
| 53 | GGP-22-41 | Phe—N2 | Thr | Phe—C3 | Thr | 120 |
| 54 | GGP-22-137 | Phe—N3 | Thr | Phe—C3 | Thr | 30 |
| 55 | GGP-22-37 | Phe—N2 | Thr | Phe—C3 | Val | 146 |

TABLE 6

Heptapeptide somatostatin analogs based on: $R^6$—Phe—Trp—Lys—Gly—$R^{11}$—$R^{12}$—$NH_2$ (SEQ ID NO:3)

| Example No. | $R^6$ | 7 | $R^8$ | $R^9$ | $R^{10}$ | $R^{11}$ | $R^{12}$ |
|---|---|---|---|---|---|---|---|
| 56 | Phe—N2 | Phe | Trp | Lys | Gly | Phe—C3 | Thr |
| 57 | Phe—N2 | Phe | Trp | Lys | Gly | Phe—C3 | Val |
| 58 | Phe—N2 | Phe | Trp | Lys | Gly | Phe—C3 | Ala |
| 59 | Phe—N2 | Phe | Trp | Lys | Gly | Phe—C3 | b-Ala |
| 60 | Phe—N2 | Phe | Trp | Lys | Gly | Phe—C3 | D2Nal |

Example 61. Detailed synthesis of PTR 3046

1 g Rink Amide MBHA resin (NOVA) (0.55 mmol/g), were swelled for 1.5 h in NMP in a reaction vessel equipped with a sintered glass bottom and placed on a shaker. The Fmoc protecting group was removed from the resin by reaction with 20% Piperidine in NMP (2 times 15 minutes, 5 ml each). Fmoc removal was monitored by Ninhydrin test. A coupling cycle was carried out with Fmoc-Thr(OtBu)-OH (4 equivalents) PyBrop (4 equivalents) DIEA (12 equivalents) in NMP (5 ml) for 0.5 hour at room temperature. Reaction completion was monitored by the qualitative Ninhydrin test (Kaiser test). Following coupling the peptide-resin was washed with NMP (3 times with 5 ml NMP, 5 ml DCM and 5 ml NMP for 2 minutes). Capping was carried out by reaction of the peptide-resin with acetic anhydride (capping mixture: HOAt 40 mg, NMP 5 ml, acetic anhydride 1 ml, DIEA 0.5 ml and DMAP(cat)) for 0.5 hours at room temperature. After capping NMP washes were carried out as above). Fmoc removal was carried out as above. Fmoc-Phe (C3)-Allyl BU was coupled(BU 2eq., PyBrop 2 eq. DIEA 6 eq., NMP 5 ml, 0.5 h. Fmoc removal was carried out as above. The peptide resin was washed as above. The peptide resin was reacted with Fmoc-Val-Cl (4 eq., Colidine 12 eq., 1 h, 38C) by double coupling. Coupling completion was monitored due to conversion of dipeptide to tripeptide (a sample of the peptide resin was cleaved and crude tripeptide was injected into HPLC (0.1% water/acetonitrile). Fmoc removal was carried out as above. Fmoc-Lys(Boc)-OH was coupled to the peptide resin by reaction conditions as for Fmoc-Thr(OtBu)-OH (see above). Coupling completion was monitored by Ninhydrin test. Fmoc-D-Trp-OH was coupled to the peptide resin with PyBrop, as described above. Following Fmoc removal, Fmoc-Tyr(tBu)-OH was coupled in the same way. Following Fmoc removal, the second building unit was introduced: Fmoc-Phe-N2(Alloc)-OH by reaction with PyBrop, as described for Fmoc-35 Phe(C3)-Allyl B. The Allyl and Alloc protecting groups were removed by reaction with $Pd(PPh_3)_4$ and acetic acid 5%, N-methylmorpholine 2.5% in chloroform, under argon, for 1.5 hours at room temperature. The peptide resin was washed as above. Cyclization was carried out with PyBOP, 3 equivalents, DIEA 6 equivalents, in NMP, at room temperature for 0.5 h. The peptide resin was washed as above. Following Fmoc removal the peptide resin was washed (DCM 3 ×5 ml), dried and cleaved from the resin by reaction with TFA 94%, water 2.5%, EDT 2.5%, TIS (tri-isopropyl-silane) 1%, at O C for 15 minutes and 1.5 hours at room temperature. The mixture was filtered and the resin was washed with a small volume of TFA. The filtrate was placed in a rotary evaporator and all the volatile components were removed. An oily product was obtained. It was triturated with ether and the ether decanted. Yellow powder was obtained. This crude product was dried. The weight of the crude product was 290 mg.

Additional examples of individual somatostatin analogs

Additional individual examples of novel somatostatin analogs produced according to the invention are summarized in Table 7.

TABLE 7

Additional somatostatin analogs synthesized.

| Example No. | $R^5$ | $R^6$ | 7 | $R^8$ | $R^9$ | $R^{10}$ | $R^{11}$ | $R^{12}$ |
|---|---|---|---|---|---|---|---|---|
| 61 | | Phe—N2 | Tyr | (D)Trp | Lys | Val | Phe—C3 | |
| 62 | | Phe—N2 | Tyr | (D)Trp | Lys | Val | Phe—C3 | |
| 63 | | Phe—N2 | pNO$_2$Phe | (D)Trp | Lys | Val | Phe—C3 | Thr |
| 64 | | Phe—N2 | Tyr | (D)Trp | Lys | (D)Val | Phe—C3 | Thr |
| 65 | | Phe—N2 | pClPhe | (D)Trp | Lys | Val | Phe—C3 | Thr |
| 66 | | Phe—N2 | Nal | (D)Trp | Lys | Val | Phe—C3 | Thr |
| 67 | (D)Phe | Phe—N2 | Tyr | (D)Trp | Lys | (D)Val | Phe—C3 | |

Libraries of Somatostatin analogs

Position numbers of amino acids in the somatostatin sequence are based on the native somatostatin peptide (SRIF-14, Raynor et. al. ibid).

Example 68: VH-SST1 library

The library was designed to contain 40 backbone cyclic peptides in five final sub-libraries, each containing 8 different peptides.

Before the last coupling step ($R^5$), the resin was split into 5 portions, coupling was performed for each portion with different AA and left as separate sub-libraries for the following steps. These five portions are the sub-libraries as described in the table 8 which indicates all the residues used at each position for generation of the 40 analogs.

TABLE 8

The composition of VH-SST1 library

| Sub-library | Residues per position | | | | | | | |
|---|---|---|---|---|---|---|---|---|
| | $R^5$ | $R^6$ | $R^7$ | $R^8$ | $R^9$ | $R^{10}$ | $R^{11}$ | $R^{12}$ |
| A | DPhe | Gly-C2 | Phe | DTrp | Lys | Gly | Gly-N2 | Val |
| B | Pro | | | Leu | Pro | Val | | |
| C | Val | | | | | | | |
| D | Leu | | | | | | | |
| E | Gly | | | | | | | |

Example 69: IG-SST1 library

In this library, the bridge was constant between position 6 with Gly-C2 and position 10 with Gly-N2. The library contains 36 peptides in 4 sub-libraries, which differ in their $R^5$ residue. The composition of this library is shown in table 9.

TABLE 9

The composition of IG-SST1 library

| Sub-library | Residues per position | | | | | | | |
|---|---|---|---|---|---|---|---|---|
| | $R^5$ | $R^6$ | $R^7$ | $R^8$ | $R^9$ | $R^{10}$ | $R^{11}$ | $R^{12}$ |
| A | DPhe | Gly-C2 | Phe | DTrp | Lys | Gly-N2 | Phe | Val |
| B | Phe | | | Phe | | | Ala | |
| C | Dtrp | | | Leu | | | Leu | |
| D | Trp | | | | | | | |

Example 70: YS-SST1 library

This library represents 16 analogs in 4 sub-libraries as described in table 10. The sub-libraries are defined by four different bridge groups (between position $R^6$ and position $R^{11}$ or $R^{10}$), and each sub-library contains four analogs.

TABLE 10

The composition of YS-SST1 library

| Sub-library | Residues per position | | | | | | | |
|---|---|---|---|---|---|---|---|---|
| | $R^5$ | $R^6$ | $R^7$ | $R^8$ | $R^9$ | $R^{10}$ | $R^{11}$ | $R^{12}$ |
| A1–2 | DPhe | Gly-C1 Gly-C2 | Phe | Dtrp | Lys | Thr | Gly-N2 Gly-N3 | Thr |
| A3–4 | DPhe | Gly-N2 Gly-N3 | Phe | Dtrp | Lys | Thr | Gly-C1 Gly-C2 | Thr |
| B1–2 | DPhe | Gly-C2 Gly-C2 | Phe | Dtrp | Lys | Gly-N2 Gly-N3 | Phe | Thr |
| B3–4 | DPhe | Gly-N1 Gly-N3 | Phe | Dtrp | Lys | Gly-C2 Gly-C2 | Phe | Thr |

Example 71: YS-SST2 library

The library contains 48 peptides in 4 sub-libraries. The sub-libraries differ in their $R^7$ residue and contain 12 peptides each. The composition of this library is shown in table 11.

TABLE 11

The composition of YS-SST2 library.

| Sub-library | Residues per position | | | | | | | |
|---|---|---|---|---|---|---|---|---|
| | $R^5$ | $R^6$ | $R^7$ | $R^8$ | $R^9$ | $R^{10}$ | $R^{11}$ | $R^{12}$ |
| A | DPhe | Gly-N3 | Phe | DTrp | Lys | Thr | Gly-C2 | Thr |
| B | | | Tyr | | | Ser | | 2Nal |
| C | | | pClPhe | | | Val | | D2Nal |
| D | | | pNO$_2$-Phe | | | Abu | | |

Example 72: YS-SST3 library

The library contains 12 peptides in 2 sub-libraries. The sub-libraries differ in their R6 building unit and contain 6 peptides each. The composition of this library is shown in table 12.

TABLE 12

The composition of YS-SST3 library

| Sub-library | Residues per position | | | | | | | |
|---|---|---|---|---|---|---|---|---|
| | $R^5$ | $R^6$ | $R^7$ | $R^8$ | $R^9$ | $R^{10}$ | $R^{11}$ | $R^{12}$ |
| A | DPhe | Phe-N2 | Phe | DTrp | Lys | Thr | Phe-C2 | Thr |
| B | Gly | Phe-N3 | | | | Ser | | |
| | | | | | | Gly | | |

Example 73: YS-SST4 library

This library contains 48 peptides in two sub-libraries. Sub-library B differs from A by the existence of Thr at $R^5$ position as described in Table 13.

TABLE 13

The composition of YS-SST4 library

| Sub-library | Residues per position | | | | | | | |
|---|---|---|---|---|---|---|---|---|
| | $R^{12}$ | $R^{11}$ | $R^{10}$ | $R^9$ | $R^8$ | $R^7$ | $R^6$ | $R^5$ |
| A | | Phe-C2 | DVal DAla DLeu | DLys DOrn | Trp Thi | DTyr | Gly-N2 Gly-N3 | Phe |
| B | Thr | Phe-C2 | DVal DAla DLeu | DLys DOrn | Trp Thi | DTyr | Gly-N2 Gly-N3 | Phe |

Example 74: YS-SST5 A and B libraries

These libraries were designed for optimization of bridge size and direction between positions 6 and 11 with simultaneous determination of the influence of various Naphthylalanine residues at position 5. The YS-SST-5A library consists of 4 sub-libraries with 16 peptides in each. The YS-SST-5B library, represents a simplified synthetic scheme of sub-libraries C and D, consisting of 8 sub-libraries of 4 peptides each. The library synthesis is illustrated in the following scheme.

YS5A LIBRARY

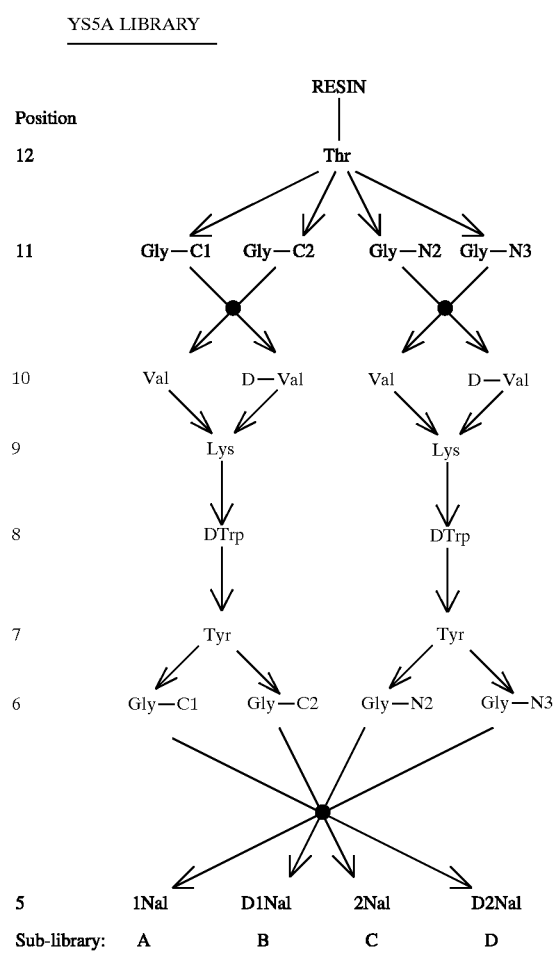

YS5B LIBRARY

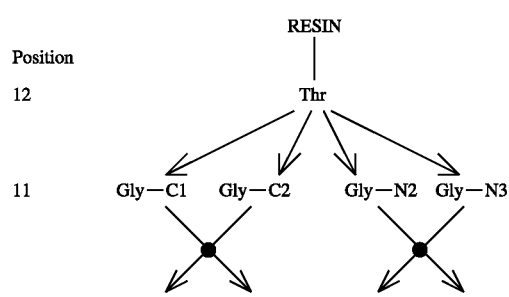

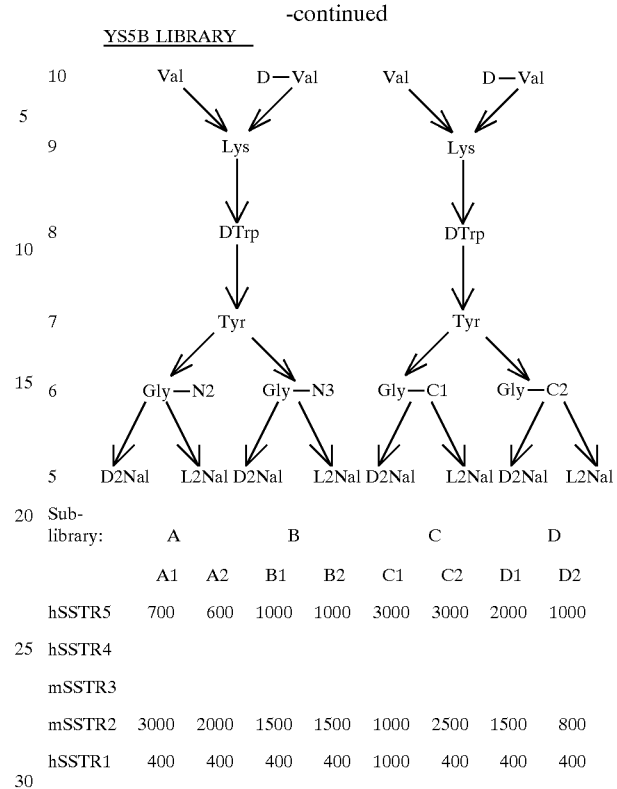

|  | A1 | A2 | B1 | B2 | C1 | C2 | D1 | D2 |
|---|---|---|---|---|---|---|---|---|
| hSSTR5 | 700 | 600 | 1000 | 1000 | 3000 | 3000 | 2000 | 1000 |
| hSSTR4 |  |  |  |  |  |  |  |  |
| mSSTR3 |  |  |  |  |  |  |  |  |
| mSSTR2 | 3000 | 2000 | 1500 | 1500 | 1000 | 2500 | 1500 | 800 |
| hSSTR1 | 400 | 400 | 400 | 400 | 1000 | 400 | 400 | 400 |

Example 75: VH-SST6 library

This library, which contains 24 hexapeptides, is described in table 14. Two different Phe-building units were incorporated at position $R^6$ with additional diversity at positions $R^7$, $R^8$ and $R^9$. The peptides were cyclized between the backbone of positions $R^6$ and $R^{10}$. Amino acids at positions 5 and 12 were omitted.

TABLE 14

The composition of VH-SST6 library
Residues per position

| $R^5$ | $R^6$ | $R^7$ | $R^8$ | $R^9$ | $R^{10}$ | $R^{11}$ | $R^{12}$ |
|---|---|---|---|---|---|---|---|
|  | Phe-C1 | Phe | DTrp | Lys |  | Gly-C2 | Phe |
|  | Phe-C2 | pNO$_2$Phe | DThi | Orn |  |  |  |
|  |  | Phg |  |  |  |  |  |

Example 76: VH-SST7 and VH-SST7A library

These libraries each contain 290304 backbone-cyclic peptides in 45 sub-libraries. The peptides were synthesized on non-cleavable resin (TentaGel-NH2), yielding bead-attached peptides for screening in solid-phase-assays. The composition of these libraries are descried in table VIII. The libraries differ from one another only in that VH-SST7 contains Trp at position 8, whereas VH-SST7A contains D-Trp at the same position.

TABLE 15

Composition of VH-SST7 library.

| Position | $R^5$ | $R^6$ | $R^7$ | $R^8$ | $R^9$ | $R^{10}$ | $R^{11}$ | $R^{12}$ |
|---|---|---|---|---|---|---|---|---|
| Groups | A | B | C | D | E | F | G | H |
| 1 | DPhe | Gly-N2 | Phe | Trp or D-Trp | Lys | Thr | Gly-C1 | Thr |
| 2 | Phg | Gly-N3 | Tyr | Tic | Arg | Val | Gly-C2 | Ser |
| 3 | 1Nal | Phe-N2 | Phg | | | Ser | Gly-C3 | Val |
| 4 | D1Nal | Phe-N3 | pClPhe | | | Abu | Phe-C1 | 1Nal |
| 5 | 2Nal | Ala-N2 | pFPhe | | | | Phe-C2 | D1Nal |
| 6 | D2Nal | Ala-N3 | pNO$_2$Phe | | | | Phe-C3 | 2Nal |
| 7 | Thi | | | | | | | D2Nal |
| 8 | DThi | | | | | | | |
| 9 | pClPhe | | | | | | | |
| 10 | pFPhe | | | | | | | |
| 11 | pNO$_2$Phe | | | | | | | |
| 12 | Des | | | | | | | Total |
| Groups | 12 | 6 | 6 | 2 | 2 | 4 | 6 | 7 | 45 |
| Pept. per group | 24192 | 12096 | 12096 | 145152 | 145152 | 72576 | 12096 | 41472 | 290304 |

The sub-libraries are named for their defined position: $A^1$, $A^2$, ... $A^n$, $B^1$ ... $B^n$, ... $H^1$ ... $H^n$. For each group, positions other than the defined one, contain mixture of amino acids. In each coupling step, each non-defined position gets a mixture of amino acids (total 1 molar equivalent of amino acids in each step in order to force the completion of each amino acid coupling and to eliminate kinetic effects, yielding non-equal presentation of peptides), that will be present at this position. Identification of the most active sub-library in each of the A to H group, by solid-phase assay, will lead to the composition of most active backbone-cyclic peptide from the 290304 peptides presented in the library.

Example 77: YS-SST6 library

This library comprises 128 backbone-cyclized somatostatin analogs in 8 sub-libraries described in table 16. Two basic cyclizations were used: position 3 to position 7 and position 2 to position 6. Each sub-library differs in the bridge location, bridge type and direction or amino acid at position 1 (Ala or D2Nal).

one another in spanning different parts of the SRIF structure was synthesized in parallel. Each octapeptide sub-library is shifted from the next by one residue. Thus, the first sub-library spands residues 7 to 14 the SRIF, the second sub-library spans residues 6 to 13 of SRIF and so on. This library comprises a total of 14 overlapping backbone-cyclized octapeptides with a shift of one residue between each sub-library.

The synthesis is achieved by simultaneous synthesis of the analogs from different starting points, such that the coupling of the building units is performed for all the sub-libraries at the same time. In all these sub-libraries the backbone cyclization is accomplished between one Glycine-C2 unit distal to the N terminal of the peptide sequence and one Glycine N3 unit proximal to the N terminal enc of the peptide sequence.

Library IG-SST9 (Sublibraries A-G, SEQ ID NOS: 4–10, respectively) is represented in the following scheme:

TABLE 16

Structure of YS-SST6 sub-libraries. Residues per position

| Sub-library | $R^1$ | $R^2$ | $R^3$ | $R^4$ | $R^5$ | $R^6$ | $R^7$ | $R^8$ | $R^9$ |
|---|---|---|---|---|---|---|---|---|---|
| A1 | Ala | Gly | Gly-C1 Gly-C2 | Lys Arg | Asn DAsn | Phe | Gly-N2 Gly-N3 | DTrp | Lys |
| A2 | D2Nal | Gly | Gly-C1 Gly-C2 | Lys Arg | Asn DAsn | Phe | Gly-N2 Gly-N3 | DTrp | Lys |
| A3 | Ala | Gly | Gly-N2 Gly-N3 | Lys Arg | Asn DAsn | Phe | Gly-C1 Gly-C2 | DTrp | Lys |
| A4 | D2Nal | Gly | Gly-N2 Gly-N3 | Lys Arg | Asn DAsn | Phe | Gly-C1 Gly-C2 | DTrp | Lys |
| B1 | Ala | Gly-C1 Gly-C2 | Gly | Lys Arg | Asn DAsn | Gly-N2 Gly-N3 | Phe | DTrp | Lys |
| B2 | D2Nal | Gly-C1 Gly-C2 | Gly | Lys Arg | Asn DAsn | Gly-N2 Gly-N3 | Phe | DTrp | Lys |
| B3 | Ala | Gly-N2 Gly-N3 | Gly | Lys Arg | Asn DAsn | Gly-C1 Gly-C2 | Phe | DTrp | Lys |
| B4 | D2Nal | Gly-N2 Gly-N3 | Gly | Lys Arg | Asn DAsn | Gly-C1 Gly-C2 | Phe | DTrp | Lys |

Example 78: IG-SST9 library

In order to more systematically test the necessity of any given frame in the SRIF sequence for biological activity of the analogs, a library of octapeptide analogs that differ from IG-SST9 Library

| Position | A | B | C | D | E | F | G |
|---|---|---|---|---|---|---|---|
| 14 | Phe | | | | | | |
| 13 | Ser | Ser | | | | | |
| 12 | GC2 | GC2 | Thr | | | | |
| 11 | Phe | Phe | Phe | Phe | | | |
| 10 | Thr | Thr | GC2 | GC2 | Thr | | |
| 9 | Lys | Lys | Lys | Lys | Lys | Lys | |
| 8 | Trp/DTrp | Trp/DTrp | Trp/DTrp | Trp/DTrp | Trp/DTrp | Trp/DTrp | Trp/DTrp |
| 7 | GN3 | GN3 | Phe | Phe | GC2 | GC2 | GC2 |
| 6 | | Phe | Phe | Phe | Phe | Phe | Phe |
| 5 | | | GN3 | GN3 | Asn | Asn | Asn |
| 4 | | | | Lys | Lys | Lys | Lys |
| 3 | | | | | GN3 | GN3 | GN3 |
| 2 | | | | | | Gly | Gly |
| 1 | | | | | | | Ala |

Example 79: SST14 library (SEQ ID NO: 11)

Different Phenylalanine-building units (PheBU: Phe-N2, Phe-N3, Phe-C2, Phe-C3), are used in this library as bridging arms for the generation of backbone cyclized analogs of SRIF sequence 4–11 (sub-library D in IG-SST9 library). In addition, the non bridging Phe residue (position 6 or 7), is substituted with various Phe and Nal derivatives: DPhe, pNO$_2$Phe, pClPhe, pFPhe, Phenylglycine (Phg), DPhg, L2Nal, D2Nal. This provides library of 18 groups and 16 analogs per group as described in the following table:

TABLE 17

The composition of SST14 library
Residues per position

| $R^4$ | $R^5$ | $R^6$ | $R^7$ | $R^8$ | $R^9$ | $R^{10}$ | $R^{11}$ |
|---|---|---|---|---|---|---|---|
| Lys/ | Asn | Phe | Phe | Trp/ | Lys | Thr | PheBu (4) |
| DLys | | PheBU (4) | PheBU (4) | DTrp | | | |
| | | DPhe | DPhe | | | | |
| | | pNO$_2$Phe | pNO$_2$Phe | | | | |
| | | pClPhe | pClPhe | | | | |
| | | pFPhe | pFPhe | | | | |
| | | Phg | Phg | | | | |
| | | DPhg | DPhg | | | | |
| | | L2Nal | L2Nal | | | | |
| | | D2Nal | D2Nal | | | | |

Example 80: YS-SST7 library

The library contains 48 analogs with the following composition:

TABLE 18

YS-SST7 library
Residues per position

| $R^5$ | $R^6$ | $R^7$ | $R^8$ | $R^9$ | $R^{10}$ | $R^{11}$ | $R^{12}$ |
|---|---|---|---|---|---|---|---|
| L2Nal | Gly-N3 | pCl-Phe | DTrp | Lys | Ser | Gly-C2 | Thr |
| DPhe | | Tyr | | | Thr | | L2Nal |
| | | | | | Val | | D2Nal |
| | | | | | Abu | | |

Example 81. YS-SST10 library. This library contains 5 sub-libraries with 24 peptides in each as described in the following scheme.

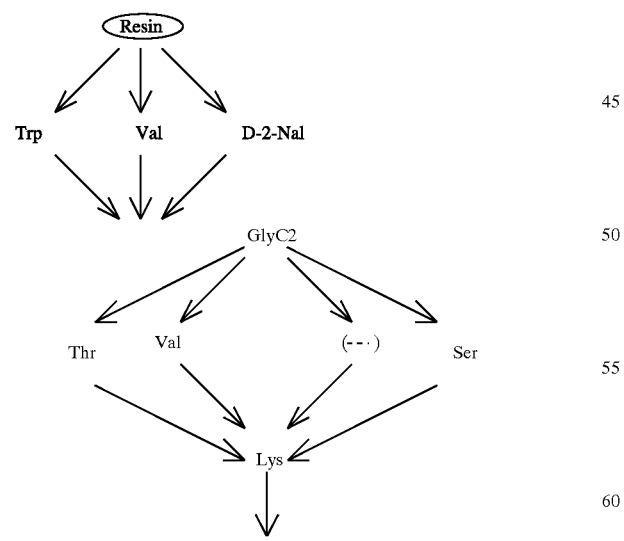

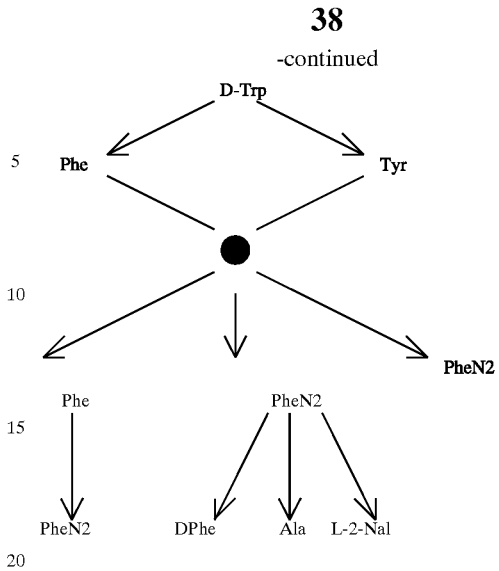

Example 82. YSS-SST12

The library, described in table 19, represents retro-backbone-cyclized analogs of somatostatin, and is composed of 6 sub-libraries, with 18 analogs in each. The different sub-libraries are defined by the type of bridge (Phe-C2$^{11}$ to Gly-N3$^6$ or Phe-N3$^{11}$ to Gly-C2$^6$), and residue at position $R^{10}$.

TABLE 19

The composition of YS-SST12 library

| Sub-library | $R^{12}$ | $R^{11}$ | $R^{10}$ | $R^9$ | $R^8$ | $R^7$ | $R^6$ | $R^5$ |
|---|---|---|---|---|---|---|---|---|
| A | | Phe-C2 | DVal | DLys | Trp | DPhe | Gly-N3 | Phe |
| B | | | DThr | | DTrp | pNH2Phep | | L2Nal |
| C | | | DGlu | | | ClDPhe | | D2Nal |
| D | | Phe-N3 | DVal | DLys | Trp | DPhe | Gly-C2 | Phe |
| E | | | DThr | | DTrp | pNH2Phe | | L2Nal |
| F | | | DGlu | | | pClDPhe | | D2Nal |

Example 83. YS-SST15 library (SEQ ID NO: 12)

This library of heptapeptides consist of 96 analogs in 8 sub-libraries defined by the residues at positions $R^6$ and $R^7$.

TABLE 20

The composition of YS-SST15 library

| Sub-library | $R^5$ | $R^6$ | $R^7$ | $R^8$ | $R^9$ | $R^{10}$ | $R^{11}$ | $R^{12}$ |
|---|---|---|---|---|---|---|---|---|
| A | | Phe-N2 | Phe | DTrp | Lys | Gly | Phe-C3 | Thr |
| B | | Phe-N3 | | Trp | DLys | | | Val |
| C | | Lys-N2 | | | | | | β-Ala |
| D | | Gly-N2 | | | | | | |
| E | | Phe-N2 | | DTrp | Lys | Gly | Phe-C3 | Thr |
| F | | Phe-N3 | Tyr | Trp | DLys | | | Val |
| G | | Lys-N2 | | | | | | β-Ala |
| H | | Gly-N2 | | | | | | |

PHYSIOLOGICAL EXAMPLES

Somatostatin analogs according to the present invention were tested for their activity in bioactivity assays in vitro and in vivo, in comparison to the following: the natural somatostatin peptide, i.e. SRIF; the known somatostatin analog Octreotide; the non cyclized somatostatin derivatives, and/or irrelevant peptides as negative controls.

Example 84: In vitro radio ligand binding assay for somatostatin.

The somatostatin analogs were tested for their potency in inhibition of the binding of $^{125}$I-Tyr$^{11}$-SRIF (based on the method described by Raynor et. al., Molecular Pharmacology 43, 838–844, 1993) to membrane preparations expressing the transmembranal somatostatin receptors (SSTR-1,2, 3,4 or 5). The receptor preparations used for these tests were either from the cloned receptors selectively and stably expressed in Chinese Hamster Ovary (CHO) cells or from cell lines naturally expressing the SSTRs. Typically, cell membranes were homogenated in Tris buffer in the presence of protease inhibitors and incubated for 30–40 minutes with $^{125}$I-Tyr$^{11}$-SRIF with different concentrations of the tested sample. The binding reactions were filtered, the filters were washed and the bound radioactivity was counted in gamma counter. Non specific binding was defined as the radioactivity remaining bound in the presence of 1 μM unlabeled SRIF-14. In order to validate positive signals of the binding tests, and to eliminate non-specific signals, samples of irrelevant peptides, such as GnRH, that were synthesized and handled using the same procedures, were tested in the same assays as negative control samples. These samples had no binding activity in any of the assays.

Example 85: Receptor binding specificity of cyclic peptide analogs.

The various somatostatin receptor subtypes are thought to be involved in different signal transduction pathways. This will have implications in terms of choosing a somatostatin analog which shows specific and selective binding to those receptor subtypes which are relevant to the disease that is to be treated. As reviewed by Reisine and Bell (Endocrine Rev. 16, 427–442, 1995), the activities of several receptor subtypes is thought to be as follows:

SSTR-1 and SSTR-2: activation of tyrosine phosphatase which can lead to inhibition of EGF receptor autosphorylation, a process that is related to the antiproliferative effect of SST.

SSTR-2: inhibition of growth hormone and gastrin release, processes that are relevant to the treatment of acromegaly and anti proliferative effects via growth factors.

SSTR-5: inhibition of insulin, lipase, amylase release, activities that are relevant to the inhibition of calcium influx and to anti-proliferative effects of SST. SSTR-3: involved in angiogenesis.

Binding of representative peptides of Examples 1–50 to different somatostatin receptors was measured in vitro, in Chinese Hamster Ovary (CHO) cells expressing the various receptors. An example of the selectivity obtained with the cyclic peptides is presented in Table 21. The $IC_{50}$ values presented are concentration required to inhibit 50% of radioactive iodinated somatostatin (SRIF-14) binding.

| PTR No. | SSTR-1 | SSTR-2 | SSTR-3 | SSTR-4 | human SSTR-5 | rat SSTR-5 |
|---|---|---|---|---|---|---|
| 3004 | | >10000 | >10000 | | | >2000 |
| 3007 | | >10000 | >10000 | | | >2000 |
| 3010 | 2500 | >10000 | >1000 | >10000 | >2000 | 500 |
| 3013 | | >10000 | >10000 | | | >2000 |
| 3016 | 2500 | | >2000 | | >2000 | 1000 |
| 3019 | | >10000 | >10000 | | | |
| 3022 | | | | | >2000 | |
| 3025 | | | >10000 | >2000 | >2000 | >2000 |
| 3034 | | | >10000 | >2000 | | >2000 |
| 3040 | 100 | >1000 | 2500 | 1000 | 2000 | 100 |
| 3043 | 2000 | 2000 | >2000 | 1000 | 400 | 400 |
| 3046 | 3000 | 500 | 500 | 250 | 22 | 30 |

The $IC_{50}$ values were calculated by testing the analogs at concentrations of $10^{-6}$, $10^{-7}$, $10^{-8}$ M in the radioligand binding assay described in example 84.

The affinities of PTR 3046 (synthetic example no. 42), to the clones SSTRs are shown in FIG. 1. The unexpected advantages of PTR 3046 over other somatostatin analogs is in its selectivity. The analog binds with high affinity to the human SSTR-5 and much less to the other SSTRS.

Furthermore, the affinity to the rat and the human SSTR5 are similar for PTR 3046, thus, drug dosages given in rat models may predict the efficacy in humans. For the sake of comparison the affinities of PTR 3046 are presented in Table 22 together with those obtained for known SST analogs.

TABLE 22

Selectivity of PTR 3046 versus known SST analogs to SSTR subtypes.

| | | IC$_{50}$ value (nM) | | | | | |
|---|---|---|---|---|---|---|---|
| Analog | Sequence | SSTR 1 | SSTR 2 | SSTR 3 | SSTR 4 | hSSTR 5 | rSSTR 5 |
| SRIF-14* | Ala$^1$-Gly$^2$-cyclo(Cys$^3$-Lys$^4$-Asn$^5$-Phe$^6$-Phe$^7$-Trp$^8$-Lys$^9$-Thr$^{10}$-Phe$^{11}$-Thr$^{12}$-Ser$^{13}$-Cys$^{14}$)-OH | 0.1 | 0.3 | 0.1 | 1.2 | 0.2 | 0.3 |
| Octreotide* | DPhe$^5$-cyclo(Cys$^6$-Phe$^7$-DTrp$^5$-Lys$^9$-Thr$^{10}$-Cys$^{11}$)-Thr$^{12}$-ol | >1000 | 0.4 | 150 | >1000 | 32 | 0.2 |
| Somatuline (BIM-23014)* | DβNal$^5$-cyclo(Cys$^6$-Tyr$^7$-DTrp$^5$-Lys$^9$-Val$^{10}$-Cys$^{11}$)-Trp$^{12}$-NH$_2$ | 800 | 2 | 6 | >1000 | 14 | 0.5 |
| RC-160** | DPhe$^5$-cyclo(Cys$^6$-Tyr$^7$-DTrp$^8$-Lys$^9$-Val$^{10}$-Cys$^{11}$)-Trp$^{12}$-NH$_2$ | 200 | 0.2 | 0.1 | 620 | 21 | 0.2 |
| BIM-23052* | DPhe$^5$-Phe$^6$-Phe$^7$-DTrp$^8$-Lys$^9$-Thr$^{10}$-Phe$^{11}$-Thr$^{12}$-NH$_2$ | 23 | 32 | 0.4 | 18 | 4 | 0.004 |
| PTR 3046 | cyclo(PheN2$^6$-Tyr$^7$-DTrp$^8$-Lys$^9$-Val$^{10}$-PheC3$^{11}$)-Thr$^{12}$-NH$_2$ | 3000 | 500 | 500 | 250 | 22 | 30 |

*Reisine and Bell (1995), Endocrine Reviews 16; 427–442.
**L. Buscail et. al. (1995), PNAS 92; 1580–1584.

Another cyclic peptide analog, PTR 3040, showed an interesting profile of selectivity. This analog shows relatively high affinity for receptor subtype SSTR-1, and very low affinity for the other receptor subtypes. While PTR 3040 showed high binding to the rat SSTR-5, its affinity to the cloned human receptor was significantly lower.

Figure 2:
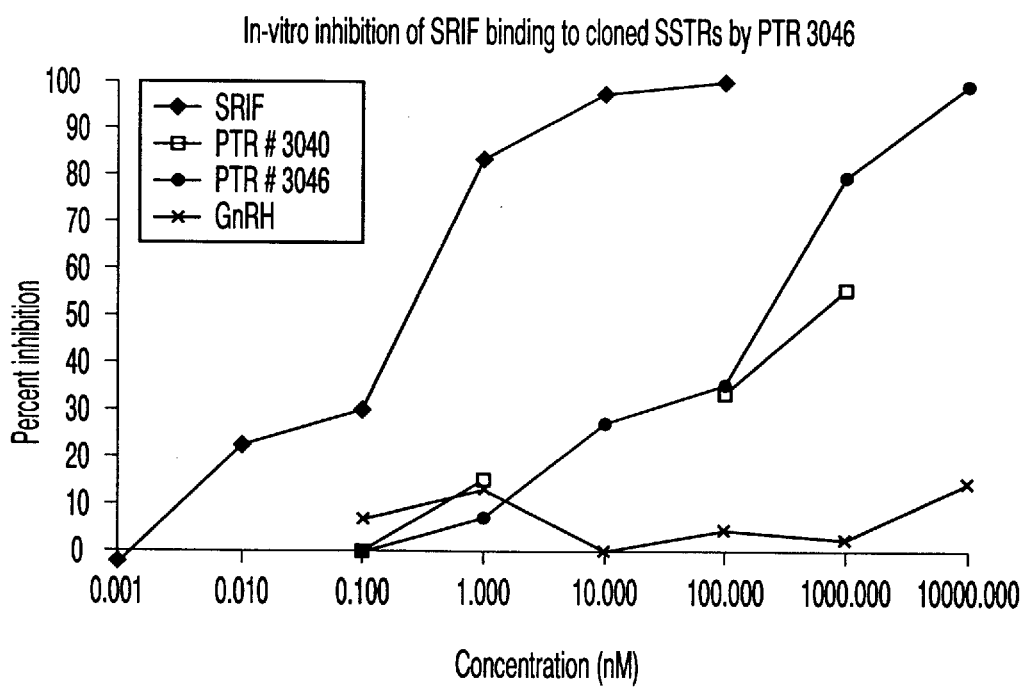
FIG. 2 is a graph showing the inhibition of somatostatin (SRIF-14) binding to the somatostatin receptors on mouse pituitary AtT20 cell line as a function of the concentration of the backbone cyclic somatostatin analogs PTR 3046 and PTR 3040.

Inhibition of $^{125}$I-SRIF binding to mouse pituitary AtT20 cells was also tested for various analogs. The results obtained with PTR 3046 and PTR 3040 are presented in FIG. 2, compared to SRIF-14. The results represent the percent inhibition per specific concentration of each of the compounds.

Example 86: Receptor binding specificity of libraries of cyclic peptide analogs.

Binding of representative sub-libraries of peptides of Examples 68–83 to different somatostatin receptors was measured in vitro, in Chinese Hamster Ovary (CHO) cells expressing the various receptors. An example of the selectivity obtained with the cyclic peptide libraries is presented in Table 23. The values presented are percent inhibition of radioactive iodinated somatostatin (SRIF-14) binding.

TABLE 23

Estimated IC$_{50}$ values (nM) for Inhibition of $^{125}$I-SRIF-14 binding to cloned SSTRs by selected backbone-cyclized sub-libraries.

| Sub-library | Pep.* | SSTR-1 | SSTR-2 | SSTR-3 | SSTR-4 | human SSTR-5 | rat SSTR-5 |
|---|---|---|---|---|---|---|---|
| VH1-A | 8 | | | | | | 8000 |
| VH1-B | 8 | | | | | | 6400 |
| VH1-C | 8 | | | | | | 7200 |
| VH1-D | 8 | | | | | | 1600 |
| VH1-E | 8 | 1600 | | >2000 | 8000 | 6400 | 640 |
| YS1-A1-2 | 4 | | | | >5000 | | 3200 |
| YS1-A3-4 | 4 | | | | >5000 | | 800 |
| YS1-B1-2 | 4 | 360 | 6000 | 3600 | 600 | 1600 | 200 |
| YS1-B1-4 | 4 | | | | >5000 | | 8000 |
| YS2-A | 12 | | | | 3600 | | 100 |
| YS2-B | 12 | | | | 3600 | | 120 |
| YS2-C | 12 | 110 | 1200 | 300 | 1000 | 100 | 25 |
| YS2-D | 12 | 960 | 300 | 4800 | 1800 | 3000 | 25 |
| YS4 | 24 | 3500 | | | 2400 | 2400 | 2000 |
| VH6 | 24 | | | | | | 7200 |
| YS5A-A | 16 | 320 | | | 6400 | 3200 | 1300 |
| YS5A-B | 16 | 1300 | | | 6400 | 1400 | |
| YS5A-C | 16 | 1300 | | 1300 | 6400 | 1300 | |
| YS5A-D | 16 | 1300 | | | 6400 | 1300 | |
| YS5B-A1 | 4 | 400 | 3000 | | | 700 | |
| YS5B-A2 | 4 | 400 | 2000 | | | 600 | |
| YS5B-B1 | 4 | 400 | 1500 | | | 1000 | |
| YS5B-B2 | 4 | 400 | 1500 | | | 1000 | |
| YS5B-C1 | 4 | 1000 | 1000 | | | 3000 | |

TABLE 23-continued

Estimated $IC_{50}$ values (nM) for Inhibition of $^{125}$I-SRIF-14 binding to cloned SSTRs by selected backbone-cyclized sub-libraries.

| Sub-library | Pep.* | SSTR-1 | SSTR-2 | SSTR-3 | SSTR-4 | human SSTR-5 | rat SSTR-5 |
|---|---|---|---|---|---|---|---|
| YS5B-C2 | 4 | 400 | 2500 | | | 3000 | |
| YS5B-D1 | 4 | 400 | 1500 | | | 2000 | |
| YS5B-D2 | 4 | 400 | 800 | | | 1000 | |

* Number of different peptides in each sub-library.

The estimated $IC_{50}$ are calculated based on the concentration of total peptides in each sub-library mixture. However, each sub-library is composed of different peptides that might have different activity. The activity of the best peptide in any given sub-library might therefore be higher (i.e., lower $IC_{50}$ value), to the extent of the given value divided by the number of peptides per sub-library. In addition, the activity values of purified individual peptides might be better due to existence of salts and impurities in the total weight of the sub-library used for calculation of the concentration.

In vivo examples:

Selected analogs were tested in-vivo, for the inhibition of growth-hormone release, amylase, lipase, gastrin, insulin, cholecystokinin (CCK), VIP and glucagon secretion in animals. Growth hormone (GH) release is related to acromegaly. Gastrin secretion is related to gastrinoma (Zollinger-ellison syndrome) and ulcer. Insulin release is related to insulinoma, hyperinsulinoma, obesity and NIDDM. Glucagon release is related to hyperglycemia, NIDDM and glucagonemia. Amylase and lipase release are related to acute and chronic pancreatitis, enterocutaneous and pancreatic fistulas and pancreatic surgery. VIP release is related to VIPoma and secretory diarrhea. In addition, the antiproliferative effects of somatostatin can be direct or indirect through GH-IGF or CCK release.

Example 87: Somatostatin biological activity assays (In vivo assays.

The in vivo biological effects of SST analogs on growth hormone, insulin and glucagon release is tested by measuring the levels of these hormones using commercially available RIA test kits. Pharmacological effects of SST in patients with neuroendocrine tumors of the gut will require determination of 5-hydroxyindole acetic acid (for carcinoid tumors) and VIP (for VIPoma). In vivo visualization of SST receptor-positive tumors is performed as described by Lambert el al. (*New England J. Med.*, 323:1246–1249 1990), following i.v. administration of radio-iodinated SST analogs.

Example 88: Resistance to biodegradation of SST analogs.

Figure 3:
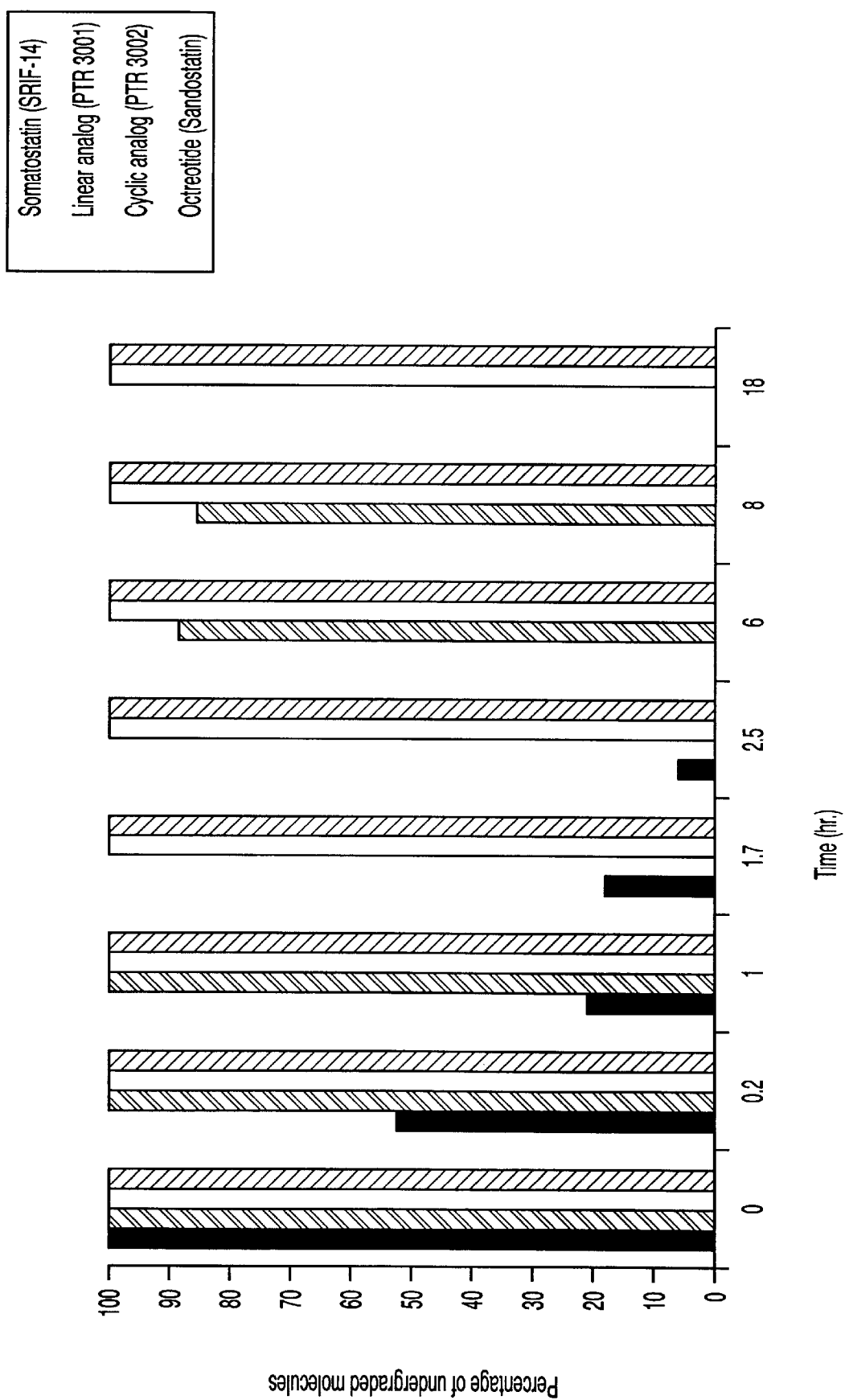
FIG. 3 is a graph showing in vitro biostability of somatostatin and three analogs thereof in human serum. The graph depicts the percentage of undegraded molecules for each of the compounds initially and after various periods of time.

The in vitro biostability of a SST cyclic peptide analog, PTR 3002, was measured in human serum, and was compared to the same sequence in a non-cyclic peptide analog (PTR 3001), to Octreotide (Sandostatin™), and to native somatostatin (SRIF). The results are shown in FIG. 3. In this assay, the cyclic peptide in accordance with the present invention is as stable as Octreotide, is more stable than the corresponding non-cyclic structure, and is much more stable than SRIF. The assay was based on HPLC determination of peptide degradation as a function of time in serum at 37° C.

Example 89: Inhibition of growth hormone release by SST analogs.

In vivo determination of the pharmacodynamic properties of cyclic peptide SST analogs was carried out in rats, according to known procedures. Inhibition of Growth Hormone (GH) release as a result of peptide administration was measured in Sprague-Dawley male rats. The SST cyclic peptide analog activity was compared in this study to SRIF or to Octreotide using 4 rats in each group. Time course profiles for GH release under constant experimental conditions were measured.

Methods

Adult male Sprague-Dawley rats, specific pathogen free (SPF), weighing 200–350 g, were maintained on a constant light-dark cycle (light from 8:00 to 20:00 h), temperature (21±3° C.), and relative humidity (55±10%). Laboratory chow and tap water were available ad libitum. On the day of the experiment, rats were anesthetized with pentobarbitone (50 mg/kg). Rats anesthetized with pentobarbitone exhibit low somatostatis levels in portal blood vessels (Plotsky, P.M., Science, 230, 461–463, 1985). A single blood sample (0.6 ml) was taken from the exposed cannulated jugular vein for the determination of the basal GH levels (−15 min.). Immediately thereafter the appropriate peptide treatment was administered. The animals received 10 mg/kg of either native somatostatin (SRIF), the synthetic analog Octreotide (Sandostatin), or the cyclic peptide analog. A physiological saline solution (0.9% NaCl) was administered as a control. All peptides were administered subcutaneously in a final volume of 0.2 ml. Further sampling was carried out at 15, 30, 60, and 90 minutes after peptide administration. Blood samples were collected into tubes containing heparin (15 units per ml of blood) and centrifuged immediately. Plasma was separated and kept frozen at −20° C. until assayed.

Rat growth hormone (rGH) [$^{125}$I] levels were determined by means of a radioimmunoassay kit (Amersham). The standard in this kit has been calibrated against a reference standard preparation (NIH-RP2) obtained from the National Institute of Diabetes and Digestive and Kidney Diseases. All samples were measured in duplicate.

The results of these experiments show that Octreotide significantly inhibits the release of growth hormone whereas the cyclic analog PTR 3046, that does not bind the SSTR-2, is not significantly different from saline in this test, as expected for a somatostatin analog which is selective for the SSTR-5 receptor subtype.

Figure 4:
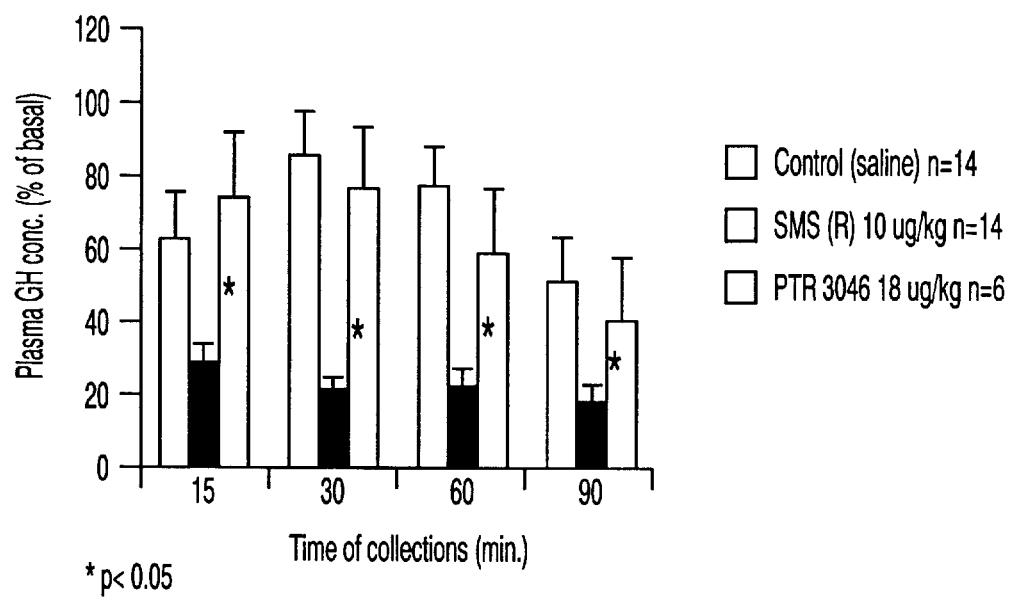
FIG. 4 is a graphical comparison of the effects of Octreotide and the backbone cyclic somatostatin analog PTR 3046 on growth hormone release in rats.

The data of these studies are summarized in FIG. 4.

Example 90: Lack of toxicity of cyclized peptide analogs.

PTR 3007 at a dose of 1.5 mg/kg was well tolerated after single intraperitoneal application. PTR 3013 was not toxic to the rats even with doses of 4 mg/kg. These two doses are several orders of magnitude higher than those needed to elicit the desired endocrine effect. The peptides dissolved in saline produced no untoward side effects on the central nervous system, cardiovascular system, body temperature, nor on the periphery of the animals. Rats were observed for 4 hours post administration of the peptides. PTR 3007 and 3013 produced no respiratory disturbances, did not result in the appearance of stereotyped behavior, or produce any changes in muscle tone. After 3 hours, postmortem examination did not detect any abnormality in the liver, kidneys, arteries and veins, gastrointestinal tract, lungs, genital system, nor the spleen.

Example 91. The in vivo effect of somatostatin analogs on glucose induced insulin release in rats.

Based on the known physiology of the native somatostatin as an inhibitor of insulin release, the aim of this study was to evaluate the effect of the backbone cyclic analog PTR 3046 on the postprandial secretion of insulin.

Experimental: Adult male Wister rats, specific pathogen free (SPF) weighing 200–220 g were used. The animals were maintained on a constant light-dark cycle (light from 8.00 to 20.00 h), Temp. (21° C.), and humidity (55%). The animals were allowed free access to food and water until 18–20 hours before the experiment, when all food (but not water) was withdrawn. The animals were housed in plastic cages with wide mesh wire bottoms to prevent coprophagia (feeding on excrement). On the day of the experiment, rats were anesthetized with pentobarbitone (60 mg/kg IP). 15 minutes after pentobarbital administration a catheter was inserted into the right external jugular vein to allow sampling of blood. Body temperature was monitored using a rectal temperature digital thermometer, and maintained at a constant level (37–37.5∞C) by heated blanket placed beneath the rat in addition to two 100W bulbs illuminating the operation table from a distance of 50 cm. After cannulation, a 0.7 ml sample of blood was drawn from the jugular vein, and transferred into tubes into which 20 IU heparin solution 5000 IU/ml was previously prepared. This blood sample was collected for the determination of the basal insulin levels. Immediately thereafter the appropriate peptide pre-treatment was administered.

The animals received the following peptides: The synthetic analog Octreotide at 10 $\mu$g/kg (n=15), the backbone cyclic peptide PTR 3046 at 7 $\mu$g/kg (n=18). Saline (0.9% NaCl) 0.2 ml was administrated as a control (n=16). All peptides were administered subcutaneously in a final volume of 0.2 ml. 10 minutes after drug administration the next blood sample was drawn, immediately after that a glucose solution was administrated IV at a final dose of 0.5 g/kg. Further sampling was carried out at 2 and 5 min. post glucose administration.

Immediately after the collection of each blood sample an appropriate volume (0.7 ml) of saline was administered IV. Blood samples were collected into tubes containing heparin (15 units per ml of a blood) and centrifuged (1500 g) immediately and plasma separated and kept frozen at −20∞C (until assayed).

Rat insulin (rIns) [$^{125}$I] levels were determined by means of rat insulin RIA kit. This kit utilizes an antibody made specifically against rat insulin (Linco). The sensitivity of the kit was 0.1 ng/ml. All samples were measured in duplicate.

Results:

Administration of 7 $\mu$g/kg of PTR 3046 led to a significant ($p<0.05$) decrease (43%) in insulin release in comparison to untreated control rats. The decrease of the insulin levels in Octreotide pretreated rats were not statistically significant in this experiment.

These results demonstrated that the backbone cyclic peptide PTR 3046 is a potent inhibitor of postprandial insulin release in vivo. Based on the present study and the manufacturer's data reported for Octreotide (ED 50 for insulin release of 26 $\mu$g/kg) it is concluded that in vivo PTR 3046 is 4 times more potent than Octreotide on insulin release.

Hyperinsulinemia is one of the etiologic factors associated with the pathology of obesity and the early stage of noninsulin dependent diabetes mellitus (NIDDM). Therefore, the potential application of PTR 3046 as an anti secretagogue on insulin release should be considered in view of the high inhibition of insulin secretion with this novel SST analog.

Figure 5:
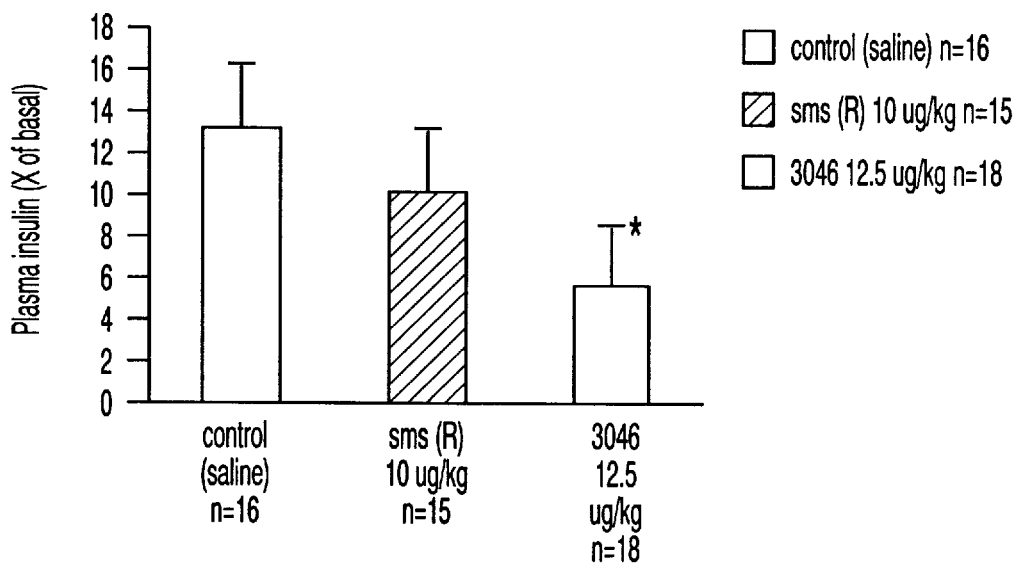
FIG. 5 is a graphical comparison of the effects of Octreotide and the backbone cyclic somatostatin analog PTR 3046 on insulin release in rats.

The data of these studies are summarized in FIG. 5.

Example 92: Effect of somatostatin analogs on bombesin stimulated plasma amylase and lipase release.

Inhibition of either insulin or amylase release has been reported (Reisine and Bell, ibid.) to be highly correlated with affinity to the SST receptor subtype SSTR-5, while i inhibition of pituitary growth hormone (GH) release, pancreatic glucagon, and gastric acid secretion were SSTR-2 mediated. Binding affinity data presented above (Example 85), demonstrated the selectivity of the cyclic heptapeptide PTR 3046 to hSSTR-5 (affinity 20 nM) in comparison to its low affinity (>1000 nM) to SSTR-1, 2, 3 and 4. Based on these results the preliminary evaluation of the physiological activity of PTR 3046 was evaluated using the in vivo model of bombesin stimulated lipase and amylase release. The dose response of PTR 3046 in terms of inhibition of amylase and lipase release in rats was measured following administration of the peptide analog at three different dosages i.e., 3 $\mu$g/kg, 12.5 $\mu$g/kg and 25 $\mu$g/kg. These doses were compared to the synthetic analog SMS-201 995 administered at a dose of 10 $\mu$g/kg.

Methods

Male Wister rats (weighing 200–220 g) were anaesthetized with pentobarbital (60 mg/kg) by the intraperitoneal (IP) route. The animals were allowed free access to food and water until 18 h before experiment, when all food (but not the water) was withdrawn. Furthermore the animals were housed in cages with wide mesh wire bottoms to prevent coprophagia (feeding on excrement).

Collection of samples

After cannulation, a 0.7 ml sample of blood was drawn from the jugular vein, and transferred into an Eppendorf tube containing 20 IU heparin solution 5000 IU/ml. One minute later the peptides were administered subcutaneously (SC in 0.2 ml of 0.9% NaCl). Control rats were pretreated with 0.2 ml of 0.9% NaCl. At time 0 (5 min. after collection of baseline blood sample-1) a bombesin infusion (50 nmol/kg/hr) was started in all animals. Additional blood samples were collected at constant time intervals of 60, 90 and 120 min. during bombesin infusion.

Treatment of samples

Blood samples were collected into ice-cold tubes containing heparin (20 IU/ml) and were centrifuged (1500 g×10 min.). Plasma samples were frozen and kept at −20° C. until assayed for amylase and lipase.

Analytical-assays

Amylase levels were measured in plasma with the commercial (Raichem™) Amylase reagent.

Lipase levels were measured in plasma with a commercial kit (Randox™).

Results

Prevention of bombesin-stimulated amylase secretion by SST analogs:

Control (saline pretreatment):

Bombesin I.V. infusion at a dose of 50 nmol/kg/h resulted in a time dependent increase of plasma amylase (by 10 fold above basal at 60 and 90 min.), and lipase (by 14 fold above basal at 60 and 90 min.).

PTR 3046:

Pretreatment with PTR 3046 resulted in significant dose dependent inhibition of bombesin induced release of plasma amylase in comparison to control rats. Inhibition was 31% at 90 min. and 23% at 120 min. for 3 μg/kg, and 60% at 90 min. and 52% at 120 min. for the dose of 25 μg/kg. Pretreatment with Octreotide at 10 μg/kg resulted in a significant inhibition 23% at these time points.

Prevention of bombesin-stimulated lipase secretion by SST analogs:

PTR 3046:

Pretreatment with PTR 3046 resulted in significant dose dependent inhibition of bombesin induced release of plasma amylase in comparison to control rats. Inhibition was 33% at 90 min. and 26% at 120 min. for 3 μg/kg, 30% at 90 min. and 25% at 120 min. for 12.5 μg/kg, and 51% at 90 and 35% at 120 min. for the dose of 25 μg/kg. While pretreatment with SMS at 10 μg/kg resulted in a significant inhibition of 27% and 30% at 90 and 120 min. respectively.

Similar results were obtained with PTR 3010 (data not shown).

These results demonstrate that PTR 3046 is a selective analog for SSTR-5 as shown in preliminary binding assays and physiological model of enzymes and endocrine secretion.

Bombesin induced pancreatic and gastric secretion is a common in vivo model for the evaluation of anti secretory effect of bombesin antagonist, bombesin antibodies, and somatostatin analogs.

The putative role of bombesin in several lung and gut diseases in humans suggest that drugs that inhibit the secretory effect of bombesin, like PTR 3010, and PTR 3046 could be used as pharmacotherapy for various therapeutic targets associated with bombesin, including: secretory diseases such as pancreatitis, rhinitis and gastrinoma; neurocrine cell hyperplasia diseases such as bronchopulmonary dysplasia, cystic fibrosis, and chronic bronchitis and emphysema; proliferative diseases such as prostate hypertrophy, prostate cancer, pancreatic cancer and stomach cancer.

Furthermore, portal hypertension, GI bleeding, and colorectal carcinoma could be potential applications as well.

What is claimed is:

1. A backbone cyclized somatostatin analog having the general Formula (Va):

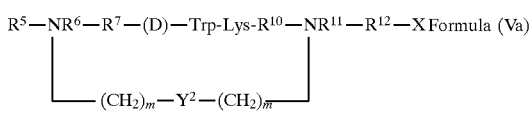

Formula (Va)

wherein m and n are 1 to 5; X designates a carboxy terminal amide or alcohol; $R^5$ is absent or is Gly, (D)- or (L)-Ala, Phe, Nal and β-Asp(Ind); $R^6$ and $R^{11}$ are independently Gly or (D)- or (L)-Phe; $R^7$ is Phe or Tyr; $R^{10}$ is absent or is Gly, Abu, Thr or Val; $R^{12}$ is absent or is Val, Thr or Nal, and $Y^2$ is selected from the group consisting of amide, thioether, thioester and disulfide.

2. The backbone cyclized peptide analog of claim 1 having the general Formula (Vb):

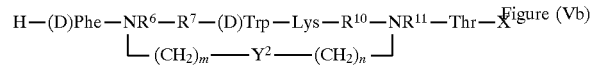

Formula (Vb)

wherein m and n are 1 to 5; X designates a carboxy terminal amide or alcohol; $R^6$ and $R^{11}$ are independently Gly or (D)- or (L)-Phe; $R^7$ is Phe or Tyr; $R^{10}$ is absent or is Gly, Abu, Thr or Val; and $Y^2$ is selected from the group consisting of amide, thioether, thioester or disulfide.

3. A backbone cyclized peptide analog having the general Formula (VIa):

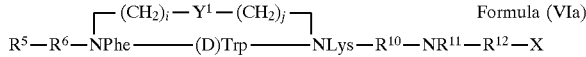

wherein i and j are independently 1 to 5; X designates a carboxy terminal amide or alcohol; $R^5$ is absent or is (D)- or (L)-Phe, Nal, or β-Asp(Ind); $R^6$ is (D) or (L)-Phe; $R^{10}$ is absent or is Gly, Abu or Thr; and $R^{11}$ is (D)- or (L)-Phe; $R^{12}$ is absent or is Thr or Nal, and $Y^1$ is selected from the group consisting of amide, thioether, thioester and disulfide.

4. The backbone cyclized peptide analog of claim 3 having the general Formula (VIb):

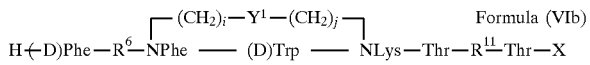

wherein i and j are independently 1 to 5; X designates a carboxy terminal amide or alcohol; $R^6$ is (D) or (L)-Phe; $R^{10}$ is absent or is Gly, Abu or Thr; and $R^{11}$ is (D)- or (L)-Phe; $R^{12}$ is absent or is Thr or Nal, and $Y^1$ is selected from the group consisting of amide, thioether, thioester and disulfide.

5. A backbone cyclized peptide analog having the general Formula (VIIa):

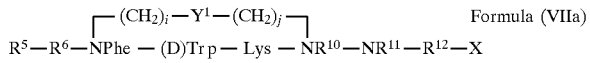

wherein i and j are independently 1 to 5; X designates a carboxy terminal amide or alcohol; $R^5$ is absent or is (D)- or (L)-Phe, Nal, or b-Asp(Ind); $R^6$ is (D) or (L)-Phe; $R^{10}$ is absent or is Gly, Abu or Thr; and $R^{11}$ is (D)- or (L)-Phe; $R^{12}$ is absent or is Thr or Nal, and $Y^1$ is selected from the group consisting of amide, thioether, thioester and disulfide.

6. The backbone cyclized peptide analog of claim 5 having the general Formula (VIIb):

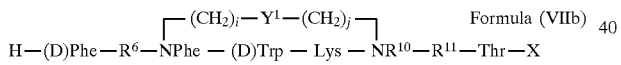

wherein i and j are independently 1 to 5; X designates a carboxy terminal amide or alcohol; $R^6$ is (D) or (L)-Phe; $R^{10}$ is absent or is Gly, Abu or Thr; and $R^{11}$ is (D)- or (L)-Phe; $R^{12}$ is absent or is Thr or Nal, and $Y^1$ is selected from the group consisting of amide, thioether, thioester and disulfide.

7. The backbone cyclized peptide analog of claim 5 having the general Formula (VIIc):

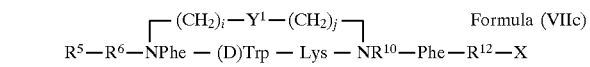

wherein i and j are independently 1 to 5; X designates a carboxy terminal amide or alcohol; $R^5$ is absent or is (D)- or (L)-Phe, Nal, or b-Asp(Ind); $R^6$ is (D) or (L)-Phe; and $R^{10}$ is absent or is Gly, Abu or Thr; $R^{12}$ is absent or is Thr or Nal, and Y1 is selected from the group consisting of amide, thioether, thioester and disulfide.

8. The backbone cyclized somatostatin analog of claim 1 having the formula NPhe-Tyr-(D)Trp-Lys-Val-NPhe-Thr-X wherein X designates a carboxy terminal acid, amide or alcohol.

9. The backbone cyclized somatostatin analog of claim 1 having the formula NPhe-Phe-(D)Trp-Lys-Thr-NPhe-Val-X wherein X designates a carboxy terminal acid, amide or alcohol.

10. A backbone cyclized somatostatin analog having the general Formula (XI):

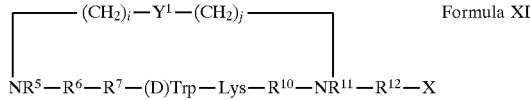

wherein i and j are independently 1 to 5; X designates a carboxy terminal amide or alcohol; $R^5$ is (D)Phe or (L)Phe, Ala or Lys; $R^6$ is absent or is Phe; $R^7$ is Tyr or Phe; $R^{10}$ is absent or Thr, Val, Ser or Abu, $R^{11}$ is Phe, Gly or Ala; $R^{12}$ is Trp, Thr, Val, 2-Nal or (D)2-Nal, and $Y^1$ is selected from the group consisting of amide, thioether, thioester and disulfide.

11. A backbone cyclized somatostatin analog having the general Formula (XIII):

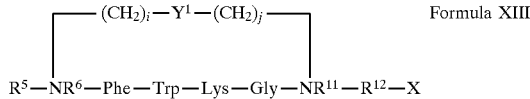

wherein i and j are independently 1 to 5; X designates a carboxy terminal amide or alcohol; $R^5$ is absent or (D)Phe or 2-Nal; $R^6$ is Phe, Gly, Lys or Ala; $R^7$ is (D)Phe, pCl(D)Phe, pNH$_2$Phe or (D)Tyr; $R^{10}$ is (D)Thr, (D)Val, (D)Ala, (D)Leu or (D)Glu; $R^{11}$ is Phe, Gly or Ala; $R^{12}$ is Thr, Val, Ala, β-Ala, (L)2-Naphthylalanine or (D)2-Naphthylalanine, and $Y^1$ is selected from the group consisting of amide, thioether, thioester and disulfide.

12. A backbone cyclized somatostatin analog having the general Formula (XIV):

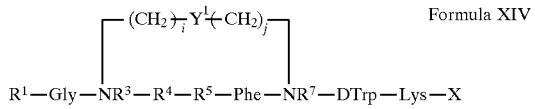

wherein i and j are independently 1 to 5; X designates a carboxy terminal amide or alcohol; $R^1$ is Ala or (D)2-Naphthylalanine; $R^2$ is Phe, Gly, Ala or Lys; $R^3$ is Phe, Gly, Ala or Lys; $R^4$ is Lys or Arg; $R^6$ is (L)Asn or (D)Asn; $R^6$ is Phe, Gly, Ala or Lys; $R^7$ is Phe, Gly, Ala or Lys, and $Y^1$ is selected from the group consisting of amide, thioether, thioester and disulfide.

13. A backbone cyclized somatostatin analog having the general formula (X):

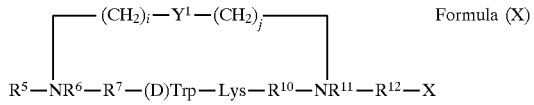

wherein i and j are independently 1 to 5; X designates a carboxy terminal amide or alcohol; $R^5$ is (D) Phe or 2-Nal; $R^6$ is Phe, Gly or Ala; $R^7$ is Tyr or pClPhe; $R^{10}$ is Thr, Val, Ser or Abu; $R^{11}$ is Phe, Gly or Ala; $R^{12}$ is Thr, Val, 2-Nal or (D)2-Nal, and $Y^1$ is selected from the group consisting of amide, thioether, thioester and disulfide.

14. The backbone cyclized somatostatin analog of claim 1 having the formula

   (i)

where $R^6$ is Phe-N2, Phe-N3, Phe-Cl, Phe-C2 or Phe-C3, and $R^{11}$ is Phe-N2, Phe-N3, Phe-C2 or Phe-C3;

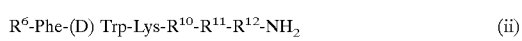   (ii)

where $R^6$ is Phe-N2 or Phe-N3, either of $R^{10}$ or $R^{12}$ is Val or Thr, and $R^{11}$ is Phe-C3; or $R^6$-Phe-Trp-Lys-Gly-$R^{11}$-$R^{12}$-NH$_2$  (iii)

where $R^6$ is Phe-N2, $R^{11}$ is Phe-C3; and $R^{12}$ is Val, Thr, Ala, b-Aal or D2Nal.

15. The backbone cyclized somatostatin analog of claim 1 having the formula $R^5$-PheN2-$R^7$-(D)Trp-Lys-$R^{10}$-PheC3-$R^{12}$-X wherein $R^5$ is absent or is D-Phe, $R^7$ is Tyr, pNO$_2$ or -pClPhe, $R^{10}$ is Val or (D)Val, $R^{12}$ is absent or is Thr, and X designates a carboxy terminal acid, amide or alcohol.

16. The backbone cyclized somatostatin analog of claim 1 specifically as

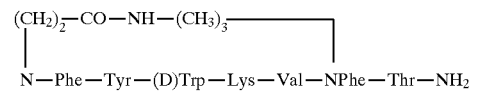

or cyclo [NPhe-Tyr-(D)Trp-Lys-Val-NPhe]-Thr-NH$_2$.

17. The backbone cyclized somatostatin analog of claim 1

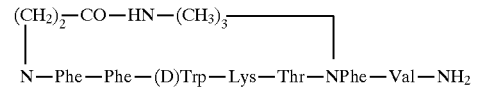

or cyclo [Nhe-Phe-(D)Trp-Lys-Thr-NPhe]-Val-NH$_2$.

* * * * *

UNITED STATES PATENT AND TRADEMARK OFFICE
CERTIFICATE OF CORRECTION

PATENT NO. : 5,770,687

DATED : June 23, 1998

INVENTOR(S) : HORNIK et al.

It is certified that error appears in the above-identified patent and that said Letters Patent is hereby corrected as shown below:

Column 57, line 28: in the second line of Formula (VIIa), change "$NR^{11}$" to --$R^{11}$--.

Column 58, line 41: after "Arg;" change "$R^6$" to --$R^5$--.

Column 60, line 17: after "cyclo" change "[Nhe" to --[NPhe--.

Signed and Sealed this

Eighteenth Day of August, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO.    : 5,770,687
DATED         : June 23, 1998
INVENTOR(S)   : Hornik et al.

It is certified that error appears in the above-identified patent and that said Letters Patent is hereby corrected as shown below:

Column 8,
Line 40, that portion of the formula reading "$NR^{11}$" should be changed to read -- $R^{11}$ --.

Column 9,
Lines 38 and 44, that portion of the formula reading "$(CH_3)_3$", should be changed to read -- $(CH_2)_3$ --.

Column 10,
Line 67, delete each occurrence of "$R^6$ is Phe, Gly, Ala or Lys;".

Column 55,
Line 61, that portion of the formula reading "$(CH_2)_m$", second occurrence, should be changed to read -- $(CH_2)_n$ --.

Column 57,
Line 5, that portion of the formula reading "$NR^{11}$" should be changed to read -- $R^{11}$ --.

Column 58,
Line 42, delete each occurrence of "$R^6$ is Phe, Gly, Ala or Lys;

Column 60,
Lines 1 and 12, that portion of the formula reading "$(CH_3)_3$", should be changed to read -- $(CH_2)_3$ --.

Signed and Sealed this

Twenty-second Day of November, 2005

JON W. DUDAS
*Director of the United States Patent and Trademark Office*